United States Patent
Sakuma et al.

(10) Patent No.: US 8,962,613 B2
(45) Date of Patent: Feb. 24, 2015

(54) P2X₄ RECEPTOR ANTAGONIST

(75) Inventors: Shogo Sakuma, Misato (JP); Masahiko Arai, Misato (JP); Kunio Kobayashi, Misato (JP); Yoshikazu Watanabe, Misato (JP); Toshiyasu Imai, Misato (JP); Kazuhide Inoue, Fukuoka (JP)

(73) Assignee: Nippon Chemiphar Co., Ltd., Chiyoda-ku, Tokyo (JP)

( * ) Notice: Subject to any disclaimer, the term of this patent is extended or adjusted under 35 U.S.C. 154(b) by 0 days.

(21) Appl. No.: 13/807,387

(22) PCT Filed: Jul. 13, 2011

(86) PCT No.: PCT/JP2011/065935
§ 371 (c)(1),
(2), (4) Date: Mar. 14, 2013

(87) PCT Pub. No.: WO2012/008478
PCT Pub. Date: Jan. 19, 2012

(65) Prior Publication Data
US 2013/0172550 A1    Jul. 4, 2013

(30) Foreign Application Priority Data
Jul. 13, 2010 (JP) ................. 2010-159186

(51) Int. Cl.
| | | |
|---|---|---|
| C07D 243/12 | (2006.01) | |
| C07D 403/10 | (2006.01) | |
| A61K 31/551 | (2006.01) | |
| A61P 25/04 | (2006.01) | |
| C07D 243/10 | (2006.01) | |
| C07D 401/10 | (2006.01) | |
| C07D 409/04 | (2006.01) | |
| C07D 413/10 | (2006.01) | |
| C07D 417/10 | (2006.01) | |
| C07D 471/04 | (2006.01) | |
| C07D 491/056 | (2006.01) | |
| C07D 401/04 | (2006.01) | |
| C07D 403/04 | (2006.01) | |
| C07D 243/24 | (2006.01) | |
| C07D 487/04 | (2006.01) | |

(52) U.S. Cl.
CPC ............ *C07D 243/10* (2013.01); *C07D 243/12* (2013.01); *C07D 403/10* (2013.01); *C07D 401/10* (2013.01); *C07D 409/04* (2013.01); *C07D 413/10* (2013.01); *C07D 417/10* (2013.01); *C07D 471/04* (2013.01); *C07D 491/056* (2013.01); *C07D 401/04* (2013.01); *C07D 403/04* (2013.01); *C07D 243/24* (2013.01); *C07D 487/04* (2013.01)
USPC .......................................... 514/220; 540/495

(58) Field of Classification Search
USPC ........................................ 540/495; 514/220
See application file for complete search history.

(56) References Cited

U.S. PATENT DOCUMENTS 8,470,814 B2 *  6/2013  Sakuma et al. ............... 514/220

* cited by examiner

*Primary Examiner* — Bruck Kifle
(74) *Attorney, Agent, or Firm* — Nixon Peabody LLP; Jeffrey L. Costellia

(57) ABSTRACT

A diazepine derivative having the following formula (III) or a pharmacologically acceptable salt thereof is used as A P2X₄ receptor antagonist:

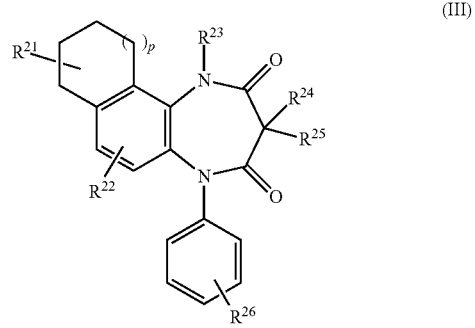

(III)

wherein each of $R^{21}$ and $R^{22}$ is hydrogen, a $C_{1-8}$ alkyl group or the like;
$R^{23}$ is hydrogen, a $C_{1-8}$ alkyl group or the like;
each of $R^{24}$ and $R^{25}$ is hydrogen, a $C_{1-8}$ alkyl group or the like;
$R^{26}$ is hydrogen, a $C_{1-8}$ alkyl group, a halogen atom, hydroxyl, nitro, cyano, phenyl optionally having one or more substituents, or a heterocyclic group optionally having one or more substituents or the like; and
p is 0 or 1.

22 Claims, No Drawings

P2X₄ RECEPTOR ANTAGONIST

FIELD OF THE INVENTION

The present invention relates to a diazepine derivative showing P2X$_4$ receptor antagonism.

BACKGROUND OF THE INVENTION

ATP receptors are basically classified into P2X family of ion-channel type receptors and P2Y family of G protein-coupled receptors. Until now, there are reported, respectively, seven sub-types (P2X$_{1-7}$) and eight sub-types (P2Y$_{1, 2, 4, 6, 11-14}$).

It has been reported that P2X$_4$ receptor (Genebank No. X87763), which is a sub-type of P2X family, is present widely in the central nervous systems (cf. Non-patent documents 1-5).

The mechanism of pathogenesis of intractable pains such as neuropathic pain is unclear. Therefore, if non-steroidal anti-inflammatory drugs (NSAIDs) and morphine are not effective, there is no other pharmacotherapy. In that case, the patient and surrounding people take up a heavy burden in mind and body. The neuropathic pain is caused by injury of peripheral or central nervous systems, for instance, post-surgery pain, cancer, spinal cord injury, herpes zoster, diabetic neuritis, or trigeminal neuralgia.

Recently, Inoue, et al. studied the involvement of P2X receptors in neuropathic pain using dorsal root ganglion neuron-injured animal model, which induces allodynia, and indicated that the nerve-injured pain (particularly, allodynia) is caused via P2X$_4$ receptors on spinal microglia (cf. Non-patent documents 6, 7, and Patent document 1).

Accordingly, compounds that inhibit the action of P2X$_4$ receptors are expected to be employed for preventing or treating nociceptive, inflammatory, and neuropathic pains.

Patent document 2 discloses that benzofuro-1,4-diazepin-2-one derivatives having the below-illustrated formula (A) show P2X$_4$ receptor antagonism:

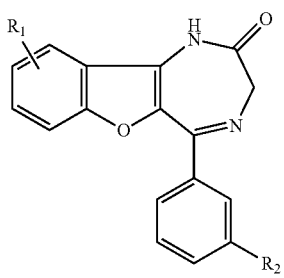

(A)

wherein R$_1$ is halogen, and R$_2$ is hydrogen, halogen, nitro, cyano, C(O)—OR$_3$, C(O)—NR$_4$R$_5$, SO$_2$—OR$_3$, or SO$_2$—NR$_4$R$_5$, or in which R$^1$ is hydrogen, and R$_2$ is halogen, nitro, cyano, C(O)—OR$_3$, C(O)—NR$_4$R$_5$, SO$_2$—OR$_3$, or SO$_2$—NR$_4$R$_5$.

Non-patent document 8 discloses that Paroxetine known as an antidepressant also shows P2X$_4$ receptor antagonism.

The present inventors have found that naphtho[1,2-e]-1,4-diazepin-2-on derivatives having the below-illustrated formula (B) showing P2X$_4$ receptor antagonism, and filed the Patent document 3.

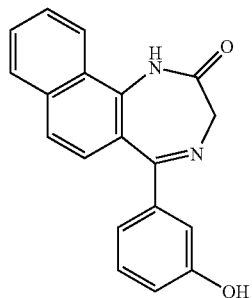

(B)

Patent document 4 discloses a naphtho[1,2-b]-1,4-diazepin-4-on derivative represented by the following formula (C).

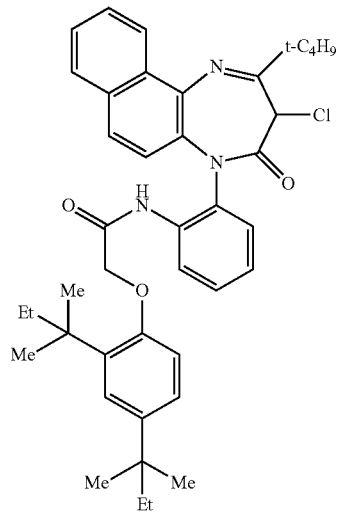

(C)

Patent document 4 describes that the compound represented by the formula (C) can be used as photographic couplers. Patent document 4, however, is silent with respect to the relation between the compound and the P2X$_4$ receptor antagonism.

Non-patent document 9 discloses a naphtho[1,2-e]-1,4-diazepin-2-on derivative represented by the following formula.

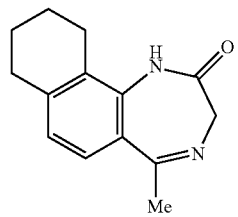 [SMILES: CC1=NCC(=O)Nc2c1ccc1c2CCCC1]

Non-patent document 9, however, is silent with respect to the relation between the compound and the P2X$_4$ receptor antagonism.

PRIOR ART DOCUMENTS

Patent Documents

Patent document 1: United States patent publication No. 20050074819
Patent document 2: WO 2004/085440
Patent document 3: WO 2008/023847
Patent document 4: Japanese Patent Publication No. 2 (1990)-304437

Non-Patent Documents

Non-patent document 1: Buell, et al. (1996) EMBO J. 15: 55-62
Non-patent document 2: Seguela, et al. (1996) J. Neurosci. 16: 448-455
Non-patent document 3: Bo, et al. (1995) FEBS Lett. 375: 129-133
Non-patent document 4: Soto, et al. (1996) Proc. Natl. Acad. Sci. USA 93: 3684-3788
Non-patent document 5: Wang, et al. (1996) Biochem. Res. Commun. 220: 196-202
Non-patent document 6: M. Tsuda, et al. (2003) Nature, 424, 778-783
Non-patent document 7: Jeffrey A. M. Coull, et al. (2005) Nature, 438, 1017-1021
Non-patent document 8: Paper Abstract of Lecture Program P3-N-114, The 49th Annual Meeting of Japanese Society for Neurochemistry (2006)
Non-patent document 9: Journal of Heterocyclic Chemistry (1976), 13(4), 813-19

SUMMARY OF THE INVENTION

Problems to be Solved by the Invention

It is the object of the present invention to provide a diazepine derivative represented by the formula (I), which shows $P2X_4$ receptor antagonism.

Means for Solving the Problems

The present invention relates to a diazepine derivative having the following formula (I) or a pharmacologically acceptable salt thereof:

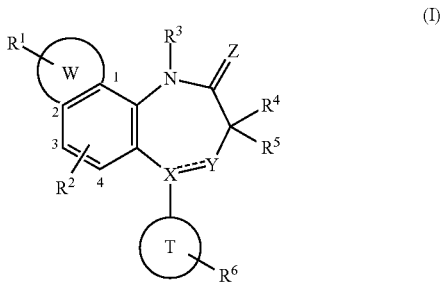

(I)

wherein each of $R^1$ and $R^2$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^3$ is hydrogen, a $C_{1-8}$ alkyl group, a $C_{2-8}$ alkenyl group, a $C_{1-8}$ alkyl group having one to three halogen atoms, or a $C_{1-3}$ alkyl group having phenyl;

each of $R^4$ and $R^5$ independently is hydrogen, a $C_{1-8}$ alkyl group, a $C_{1-8}$ alkyl group having one to three halogen atoms, a halogen atom, hydroxyl, nitro, cyano, amino, or a $C_{1-3}$ alkyl group having phenyl;

$R^6$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents;

the ring shown below is a five-membered to eight-membered non-aromatic ring optionally comprising one or two heteroatoms selected from N, S, and O, and being condensed with the benzene ring at the positions of 1 and 2 of the benzene ring;

the ring shown below is an aromatic ring selected from the group consisting of benzene ring, naphthalene ring, thiophene ring, pyridine ring, pyrimidine ring, indole ring, indazole ring, benzotriazole ring, benzisoxazole ring, benzimidazole ring, and quinoline ring;

Z is O or S;

when X is N, Y is C=O or C=S, and the double line consisting of a solid line and a broken line is a single bond; and when X is C, Y is N, and the double line consisting of a solid line and a broken line is a double bond.

The invention also relates to a diazepine derivative having the following formula (II) or a pharmacologically acceptable salt thereof:

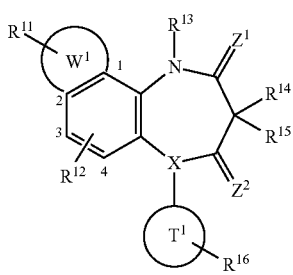

(II)

wherein each of $R^{11}$ and $R^{12}$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^{13}$ is hydrogen, a $C_{1-8}$ alkyl group, a $C_{2-8}$ alkenyl group, a $C_{1-8}$ alkyl group having one to three halogen atoms, or a $C_{1-3}$ alkyl group having phenyl;

each of $R^{14}$ and $R^{15}$ independently is hydrogen, a $C_{1-8}$ alkyl group, a $C_{1-8}$ alkyl group having one to three halogen atoms, a halogen atom, hydroxyl, nitro, cyano, amino, or a $C_{1-3}$ alkyl group having phenyl;

$R^{16}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents;

the ring shown below is a five-membered to eight-membered non-aromatic ring optionally comprising one or two heteroatoms selected from N, S, and O, and being condensed with the benzene ring at the positions of 1 and 2 of the benzene ring;

the ring shown below is an aromatic ring selected from the group consisting of benzene ring, naphthalene ring, thiophene ring, pyridine ring, pyrimidine ring, indole ring, indazole ring, benzotriazole ring, benzisoxazole ring, benzimidazole ring, and quinoline ring; and

each of $Z^1$ and $Z^2$ independently is C or S.

The invention further relates to a diazepine derivative having the following formula (III) or a pharmacologically acceptable salt thereof:

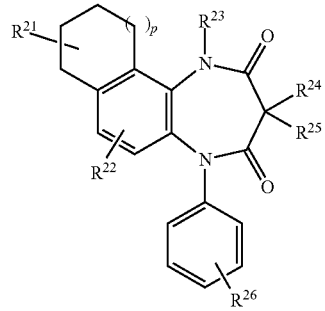

(III)

wherein each of $R^{21}$ and $R^{22}$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^{23}$ is hydrogen, a $C_{1-8}$ alkyl group, a $C_{2-8}$ alkenyl group, a $C_{1-8}$ alkyl group having one to three halogen atoms, or a $C_{1-3}$ alkyl group having phenyl;

each of $R^{24}$ and $R^{25}$ independently is hydrogen, a $C_{1-8}$ alkyl group, a $C_{1-8}$ alkyl group having one to three halogen atoms, a halogen atom, hydroxyl, nitro, cyano, amino, or a $C_{1-3}$ alkyl group having phenyl;

$R^{26}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, sulfamoyl, phenyl optionally having one or more substituents, or a heterocyclic group optionally having one or more substituents; and p is 0 or 1.

The invention also relates to a $P2X_4$ receptor antagonist containing a compound represented by the formula (I), (II), or (III), or its pharmacologically acceptable salt as an active ingredient.

The invention further relates to a preventive or therapeutic agent for neuropathic pains containing a compound represented by the formula (I), (II), or (III), or its pharmacologically acceptable salt as an active ingredient.

THE EMBODIMENTS OF THE INVENTION

The present invention is described below in more detail.
In the compound of the present invention represented by the formula (I), the alkyl group having 1 to 8 carbon atoms for $R^1$, $R^2$, $R^3$, $R^4$, $R^5$, and $R^6$ can be methyl, ethyl, propyl, isopropyl, butyl, isobutyl, t-butyl, pentyl, or hexyl.

The alkenyl group having 2 to 8 carbon atoms for $R^1$, $R^2$, $R^3$, and $R^6$ can be allyl.

The alkyl group having 1 to 8 carbon atoms substituted with 1 to 3 halogen atoms for $R^1$, $R^2$, $R^3$, $R^4$, $R^5$, and $R^6$ can be methyl, ethyl, propyl, isopropyl, butyl, or t-butyl substituted with 1 to 3 halogen atoms such as 1 to 3 fluoro, chloro, or bromo atoms, and preferably is trifluoromethyl, chloromethyl, 2-chloroethyl, 2-bromoethyl, or 2-fluoroethyl.

The alkyl group having 1 to 3 carbon atoms substituted with phenyl for $R^3$, $R^4$, and $R^5$ can be benzyl.

The alkoxy group having 1 to 8 carbon atoms for $R^1$, $R^2$, and $R^6$ can be methoxy, ethoxy, propoxy, isopropoxy, butoxy, isobutoxy, t-butoxy, pentyloxy, or hexyloxy.

The alkoxy group having 1 to 8 carbon atoms substituted with 1 to 3 halogen atoms for $R_1$, $R^2$, and $R^6$ can be methoxy, ethoxy, propoxy, isopropoxy, butoxy, isobutoxy, or t-butoxy substituted with 1 to 3 halogen atoms such as 1 to 3 fluoro, chloro, or bromo atoms, and preferably include trifluoromethoxy, chloromethoxy, 2-chloroethoxy, 2-bromoethoxy, or 2-fluoroethoxy.

The halogen atom for $R^1$, $R^2$, $R^4$, $R^5$, and $R^6$ can be fluoro, chloro, or bromo atom.

The alkylamino group having 1 to 8 carbon atoms for $R^1$, $R^2$, and $R^6$ can be methylamino or ethylamino.

The dialkylamino group having 2 to 8 carbon atoms for $R^1$, $R^2$, and $R^6$ can be dimethylamino or diethylamino.

The acylamino group having 2 to 8 carbon atoms for $R^1$, $R^2$, and $R^6$ can be acetylamino.

The acylamino group having 2 to 8 carbon atoms substituted with 1 to 3 halogen atoms for $R^1$, $R^2$, and $R^6$ can be trifluoromethylcarbonylamino.

The alkylsulfonylamino group having 1 to 8 carbon atoms for $R^1$, $R^2$, and $R^6$ can be methylsulfonylamino.

The acyl group having 2 to 8 carbon atoms for $R^1$, $R^2$, and $R^6$ can be acetyl.

The alkoxycarbonyl group comprising an alkoxy moiety having 1 to 8 carbon atoms for $R^1$, $R^2$, and $R^6$ can be methoxycarbonyl, or ethoxycarbonyl.

The alkylthio group having 1 to 8 carbon atoms for $R^1$, $R^2$, and $R^6$ can be methylthio.

The alkylsulfinyl group having 1 to 8 carbon atoms for $R^1$, $R^2$, and $R^6$ can be methylsulfinyl.

The alkylsulfonyl group having 1 to 8 carbon atoms for $R^1$, $R^2$, and $R^6$ can be methylsulfonyl.

With respect to the phenyl optionally having one or more substituents for $R^6$, the substituent preferably is an alkyl group having 1 to 8 carbon atoms (such as methyl, ethyl), an alkyl group having 1 to 8 carbon atoms substituted with 1 to 3 halogen atoms (such as trifluoromethyl), a halogen atom (such as fluoro atom), and cyano. The heterocyclic group optionally having one or more substituents for $R^6$ preferably is tetrazolyl, triazolyl, pyridyl, imidazolyl, oxazolyl, or triazolyl. The heterocyclic group can also be oxadiazolyl.

With respect to the heterocyclic group optionally having one or more substituents for $R^6$, the substituent preferably is an alkyl group having 1 to 8 carbon atoms (e.g., methyl, ethyl), an alkyl group having 1 to 8 carbon atoms substituted with 1 to 3 halogen atoms (such as trifluoromethyl), a halogen atom (such as fluoro atom), cyano, and oxo. The substituent can also be phenyl.

The ring shown below can be tetrahydronaphthalene, indan, indoline, tetrahydroquinoline, or tetrahydroisoquinoline.

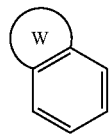

$R^1$, $R^2$, and $R^6$ in the formula (I) can be the same or different two or more substituents attached to the rings to which $R^1$, $R^2$, and $R^6$ are attached.

Examples of $R^{11}$ to $R^{16}$ in the formula (II) and $R^{21}$ to $R^{26}$ in the formula (III) are the same as the examples of the alkyl group having 1 to 8 carbon atoms, the alkenyl group having 2 to 8 carbon atoms, the alkyl group having 1 to 8 carbon atoms substituted with 1 to 3 halogen atoms, the alkyl group having 1 to 3 carbon atoms substituted with phenyl, the alkoxy group having 1 to 8 carbon atoms, the alkoxy group having 1 to 8 carbon atoms substituted with 1 to 3 halogen atoms, the halogen atom, the alkylamino group having 1 to 8 carbon atoms, the dialkylamino group having 2 to 8 carbon atoms, the acylamino group having 2 to 8 carbon atoms, the acylamino group having 2 to 8 carbon atoms substituted with 1 to 3 halogen atoms, the alkylsulfonylamino group having 1 to 8 carbon atoms, the acyl group having 2 to 8 carbon atoms, the alkoxycarbonyl group comprising an alkoxy moiety having 1 to 8 carbon atoms, the alkylthio group having 1 to 8 carbon atoms, the alkylsulfinyl group having 1 to 8 carbon atoms, the alkylsulfonyl group having 1 to 8 carbon atoms, the phenyl optionally having one or more substituents, and the heterocyclic group optionally having one or more substituents for $R^1$ to $R^6$ in the formula (I).

With respect to the heterocyclic group optionally having one or more substituents for $R^{16}$ in the formula (II) and $R^{26}$ in the formula (III), the examples of the substituents are the same as the examples of the alkyl group having 1 to 8 carbon atoms, the alkyl group having 1 to 8 carbon atoms substituted with 1 to 3 halogen atoms, the halogen atoms, the alkylamino group having 1 to 8 carbon atoms, and the dialkylamino group having 2 to 8 carbon atoms for $R^1$ to $R^6$ in the formula (I).

The ring shown below can be tetrahydronaphthalene, indan, indoline, tetrahydroquinoline, or tetrahydroisoquinoline.

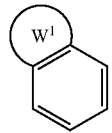

$R^{11}$, $R^{12}$, and $R^{16}$ in the formula (II) can be the same or different two or more substituents attached to the rings to which $R^{11}$, $R^{12}$, and $R^{16}$ are attached.

$R^{21}$, $R^{22}$, and $R^{26}$ in the formula (III) can be the same or different two or more substituents attached to the rings to which $R^{21}$, $R^{22}$, and $R^{26}$ are attached.

The compound of the present invention of the formula (II) preferably is the following compound.

(1) A diazepine derivative having the formula (II) or a pharmacologically acceptable salt thereof, wherein $R^{11}$ is hydrogen, a $C_{1-8}$ alkyl group, a $C_{2-8}$ alkenyl group, a $C_{1-8}$ alkyl group having one to three halogen atoms, a halogen atom, hydroxyl, amino, a $C_{1-8}$ alkylamino group, a $C_{2-8}$ dialkylamino group, or a $C_{2-8}$ acylamino group.

(2) A diazepine derivative having the formula (II), a pharmacologically acceptable salt thereof or (1), wherein $R^{12}$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, or a $C_{2-8}$ acylamino group having one to three halogen atoms.

(3) A diazepine derivative having the formula (II), a pharmacologically acceptable salt thereof, (1), or (2), wherein $R^{13}$ is hydrogen, a $C_{1-8}$ alkyl group, or a $C_{1-8}$ alkyl group having one to three halogen atoms.

(4) A diazepine derivative having the formula (II), a pharmacologically acceptable salt thereof, or one of (1) to (3), wherein each of $R^{14}$ and $R^{15}$ independently is hydrogen, a $C_{1-8}$ alkyl group, or a $C_{1-8}$ alkyl group having one to three halogen atoms.

(5) A diazepine derivative having the formula (II), a pharmacologically acceptable salt thereof, or one of (1) to (4), wherein $R^{16}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, or a heterocyclic group optionally having one or more substituent.

(6) A diazepine derivative having the formula (II), a pharmacologically acceptable salt thereof, or one of (1) to (4), wherein $R^{16}$ is a heterocyclic group optionally having one or more substituents, said heterocyclic group being tetrazolyl, triazolyl, pyridyl, pyrazolyl, oxadiazolyl, isoxazolyl, pyrrolyl, pyrrolidinyl, imidazolyl, oxazolyl, or thiazolyl, and said substituents being selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

(7) A diazepine derivative having the formula (II), a pharmacologically acceptable salt thereof, or one of (1) to (4), wherein $R^{16}$ is a heterocyclic group optionally having one or more substituents, said heterocyclic group being tetrazolyl, triazolyl, pyridyl, imidazolyl, oxazolyl, or thiazolyl, and said substituents being selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, cyano, and amino.

(8) A diazepine derivative having the formula (II), a pharmacologically acceptable salt thereof, or one of (1) to (7), wherein the ring shown below is tetrahydronaphthalene, indan, indoline, tetrahydroquinoline, or tetrahydroisoquinoline.

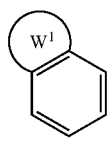

(9) A diazepine derivative having the formula (II), a pharmacologically acceptable salt thereof, or one of (1) to (8), wherein the ring shown below is benzene.

(10) A diazepine derivative having the formula (II), a pharmacologically acceptable salt thereof, or one of (1) to (9), wherein each of each of $Z^1$ and $Z^2$ is O.

The compound of the present invention of the formula (III) preferably is the following compound.

(11) A diazepine derivative having the formula (III) or a pharmacologically acceptable salt thereof, wherein $R^{21}$ is hydrogen, a $C_{1-8}$ alkyl group, a $C_{2-8}$ alkenyl group, a $C_{1-8}$ alkyl group having one to three halogen atoms, a halogen atom, hydroxyl, amino, a $C_{1-8}$ alkylamino group, a $C_{2-8}$ dialkylamino group, or a $C_{2-8}$ acylamino group.

(12) A diazepine derivative having the formula (II), a pharmacologically acceptable salt thereof or (11), wherein $R^{22}$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, or a $C_{2-8}$ acylamino group having one to three halogen atoms.

(13) A diazepine derivative having the formula (III), a pharmacologically acceptable salt thereof, (11), or (12), wherein $R^{23}$ is hydrogen, a $C_{1-8}$ alkyl group, or a $C_{1-8}$ alkyl group having one to three halogen atoms.

(14) A diazepine derivative having the formula (III), a pharmacologically acceptable salt thereof, or one of (11) to (13), wherein each of $R^{24}$ and $R^{25}$ independently is hydrogen, a $C_{1-8}$ alkyl group, or a $C_{1-8}$ alkyl group having one to three halogen atoms.

(15) A diazepine derivative having the formula (III), a pharmacologically acceptable salt thereof, or one of (11) to (14), wherein $R^{26}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, or a heterocyclic group optionally having one or more substituent.

(16) A diazepine derivative having the formula (III), a pharmacologically acceptable salt thereof, or one of (11) to (14), wherein $R^{26}$ is a heterocyclic group optionally having one or more substituents, said heterocyclic group being tetrazolyl, triazolyl, pyridyl, pyrazolyl, oxadiazolyl, isoxazolyl, pyrrolyl, pyrrolidinyl, imidazolyl, oxazolyl, or thiazolyl, and said substituents being selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

(17) A diazepine derivative having the formula (III), a pharmacologically acceptable salt thereof, or one of (11) to (14), wherein $R^{26}$ is a heterocyclic group optionally having one or more substituents, said heterocyclic group being tetrazolyl, triazolyl, pyridyl, imidazolyl, oxazolyl, or thiazolyl, and said substituents being selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, cyano, and amino.

The pharmacologically acceptable salts of the compound represented by the formula (I), (II), or (III) include a hydrochloride salt and an alkali metal (e.g., sodium, potassium, lithium) salt.

e compound of the present invention can be a geometrical isomer or an optical isomer such as an optically active substance and racemic modification, each of which is included within the scope of the invention.

$R^3$ in the formula (I), $R^{13}$ in the formula (II), and $R^{23}$ in the formula (III) can be a $C_{2-8}$ acyl group such as acetyl.

$R^6$ in the formula (I), $R^{16}$ in the formula (II), and $R^{26}$ in the formula (III) can be a $C_{3-8}$ alkoxycarbonylamino group such as tert-butoxycarbonylamino.

The rings shown below in the formulas (I) and (II) can be 2,3-dihydrobenzo[1,4]dioxin.

T    T¹

The schemes for synthesis of the compound of the invention represented by the formula (III) are shown below.

[Method 1]

(a)

(b)

(III)

In the above-illustrated formula, $R^{21}$, $R^{22}$, $R^{23}$, $R^{24}$, $R^{25}$, $R^{26}$, and p are defined above.

The compound of the invention represented by the formula (III) can be obtained by subjecting the compound represented by the formula (a) and the compound represented by the formula (b) to a ring-closing reaction in the presence of a solvent such as THF.

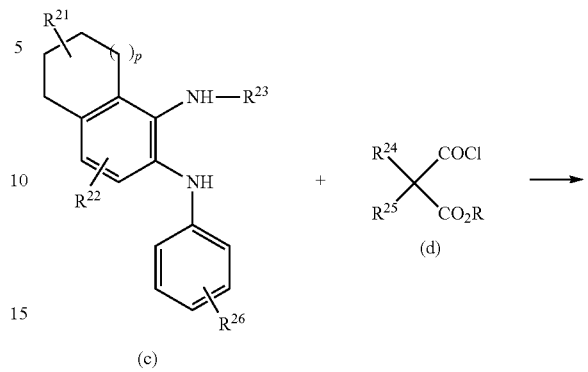

[Method 2]

(c)

(d)

(e)

(III)

In the above-illustrated formula, R is a lower alkyl group, and $R^{21}$, $R^{22}$, $R^{23}$, $R^{24}$, $R^{25}$, $R^{26}$, and p are defined above.

The compound represented by the formula (e) can be obtained by reacting the compound represented by the formula (c) with the compound represented by the formula (d) in the presence of a solvent such as chloroform. The compound of the invention represented by the formula (III) can be obtained by subjecting the obtained compound represented by the formula (e) to a ring-closing reaction in the presence of sodium hydride in a solvent such as THF.

[Method 3]

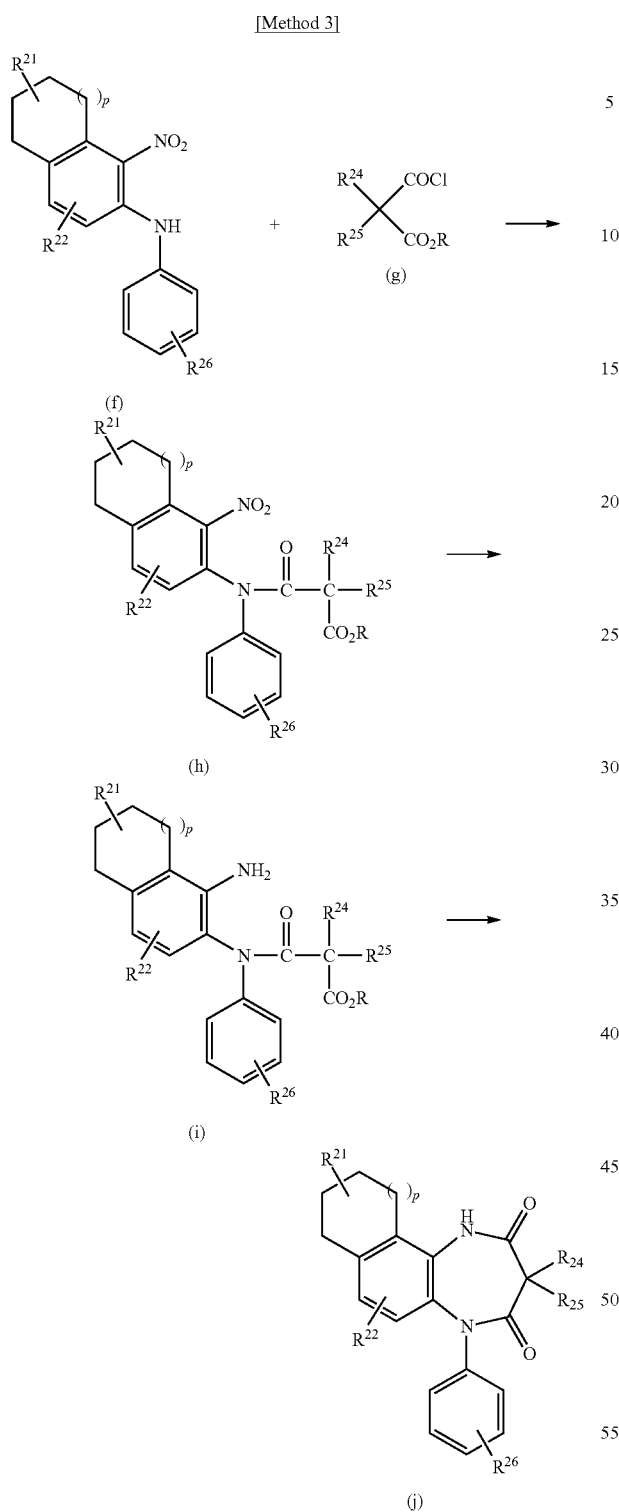

In the above-illustrated formula, R is a lower alkyl group, and $R^{21}$, $R^{22}$, $R^{24}$, $R^{25}$, $R^{26}$, and p are defined above.

The compound represented by the formula (h) can be obtained by reacting the compound represented by the formula (f) with the compound represented by the formula (g) in the presence of a solvent such as chloroform. The compound represented by the formula (I) can be obtained by subjecting the obtained compound represented by the formula (h) to a reductive reaction in the presence of a Pb catalyst in a solvent such as ethanol. The compound of the invention represented by the formula (j) can be obtained by subjecting the obtained compound represented by the formula (i) to a ring-closing reaction in the presence of a sodium alkoxide in a solvent such as ethanol.

[Method 4]

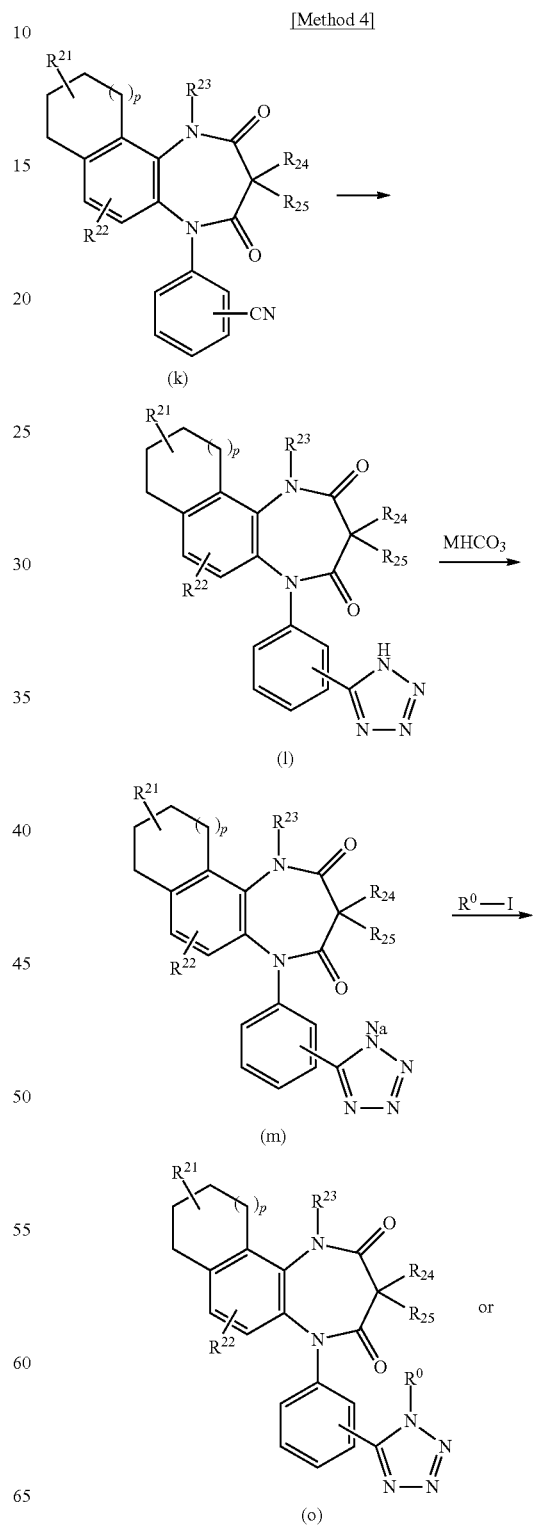

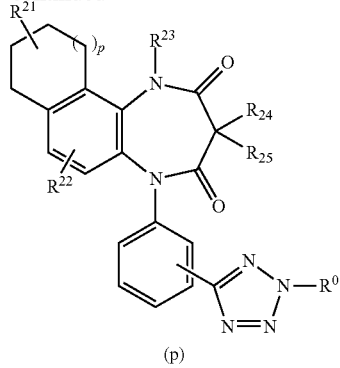

(p)

In the above-illustrated formulas, $R^0$ is a lower alkyl group, and $R^{21}$, $R^{22}$, $R^{23}$, $R^{24}$, $R^{25}$, and p are defined above.

The tetrazole compound represented by the formula (l) can be obtained by reacting the compound represented by the formula (k) with an azide compound such as tri-n-butyltin azide or sodium azide by the formula (g) in the presence of a solvent such as toluene or DMF.

The metal salt represented by the formula (m) can be obtained by reacting the tetrazole compound represented by the formula (l) with an inorganic salt such as sodium hydrogencarbonate and potassium hydrogencarbonate in the presence of a solvent such as water or ethanol.

The compound represented by the formula (O) or the formula (p) can be obtained by reacting the metal salt represented by the formula (m) with an alkyl iodide in the presence of a solvent such as water or ethanol.

The compound of the present invention represented by the formulas (I) and (II) can also be prepared by referring to the above-mentioned synthesis methods, the below described Examples, the patent documents described above, and the other known documents.

Examples of the obtained compounds of the present invention are shown below.

(Representative compound 1)

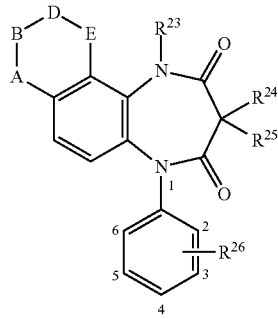

In the above-illustrated formula, A-B-D-E, $R^{23}$, $R^{24}/R^{25}$, and $R^{26}$ are shown in Tables 1 to 3.

TABLE 1

| A-B-D-E | $R^{23}$ | $R^{24}/R^{25}$ | $R^{26}$ |
|---|---|---|---|
| $CH_2-CH_2-CH_2-CH_2$ | H | H/H | 3-CN |
| $CH_2-CH_2-CH_2-CH_2$ | H | H/H | 3-OH |
| $CH_2-CH_2-CH_2-CH_2$ | H | H/H | $3-CO_2H$ |
| $CH_2-CH_2-CH_2-CH_2$ | H | H/H | $3-CONH_2$ |

TABLE 1-continued

| A-B-D-E | $R^{23}$ | $R^{24}/R^{25}$ | $R^{26}$ |
|---|---|---|---|
| $C(CH_3)_2-CH_2-CH_2-CH_2$ | H | H/H | $3,4-OCH_3$ |
| $CH_2-C(CH_3)_2-CH_2-CH_2$ | $CH_3$ | H/H | $3,4-OCH_3$ |
| $CH_2-CH_2-C(CH_3)_2-CH_2$ | $C_2H_5$ | H/H | 3-OH, 4-F |
| $CH_2-CH_2-CH_2-CH_2$ | H | H/H | $3-NH_2$ |
| $NH-CH_2-CH_2-CH_2$ | H | H/H | $3-NHCH_3$ |
| $N(CH_3)-CH_2-CH_2-CH_2$ | H | H/H | $3-CF_3$ |
| $O-CH_2-CH_2-O$ | H | H/H | $3-NHCH_2CF_3$ |
| $O-CH_2-CH_2-O$ | $CH_3$ | H/H | 2-OH, 3-OH |
| $C(CH_3)_2-CH_2-CH_2-C(CH_3)_2$ | $C_2H_5$ | H/H | $3,4,5-CH_3$ |

TABLE 2

| A-B-D-E | $R^{23}$ | $R^{24}/R^{25}$ | $R^{26}$ |
|---|---|---|---|
| $CH_2-CH_2-CH_2-CH_2$ | H | $CH_3$/H | 4-OH |
| $CH_2-CH_2-CH_2-CH_2$ | H | $CH_3/CH_3$ | $4-NH_2$ |
| $CH_2-CH_2-CH_2-CH_2$ | H | propyl/H | $4-NO_2$ |
| $C(CH_3)_2-CH_2-CH_2-CH_2$ | H | H/H | 4-CN |
| $CH_2-C(CH_3)_2-CH_2-CH_2$ | $CH_3$ | $CF_3$/H | 4-phenyl |
| $CH_2-CH_2-C(CH_3)_2-CH_2$ | $C_2H_5$ | H/H | $4-CH_2OH$ |
| $CH_2-CH_2-CH_2-CH_2$ | H | H/H | $3-CH_2OH$ |
| $NH-CH_2-CH_2-CH_2$ | H | H/H | $3-COCH_3$ |
| $N(CH_3)-CH_2-CH_2-CH_2$ | H | H/H | $3,5-OCH_3$ |
| $O-CH_2-CH_2-O$ | H | H/H | 3-OH, $4-NH_2$ |
| $O-CH_2-CH_2-O$ | $CH_3$ | H/H | $3-CH_2NH_2$ |
| $C(CH_3)_2-CH_2-CH_2-C(CH_3)_2$ | $C_2H_5$ | H/H | $3-SO_2CH_3$ |
| $CH_2-CH_2-CH_2-CH_2$ | H | $CH_3$/H | 3-isopropyl |
| $CH_2-CH_2-CH_2-CH_2$ | H | $CH_3$/H | $3-N(CH_3)_2$ |

TABLE 3

| A-B-D-E | $R^{23}$ | $R^{24}/R^{25}$ | $R^{26}$ |
|---|---|---|---|
| $CH_2-CH_2-CH_2-CH_2$ | H | $CH_3$/H | $4-COCH_3$ |
| $C(CH_3)_2-CH_2-CH_2-CH_2$ | H | propyl/H | $3,4-NH_2$ |
| $CH_2-C(CH_3)_2-CH_2-CH_2$ | H | H/H | $NHCH_3$ |
| $CH_2-CH_2-C(CH_3)_2-CH_2$ | $C_2H_5$ | H/H | $3-NHCH_2CF_3$ |
| $CH_2-CH_2-CH_2-CH_2$ | H | H/H | $3-NHCOCH_3$ |
| $NH-CH_2-CH_2-CH_2$ | H | H/H | $3-SO_2CH_3$ |
| $N(CH_3)-CH_2-CH_2-CH_2$ | H | H/H | $4-CH_3$ |
| $O-CH_2-CH_2-O$ | H | H/H | 4-isopropyl |
| $O-CH_2-CH_2-O$ | $CH_3$ | H/H | 3-phenyl |
| $C(CH_3)_2-CH_2-CH_2-C(CH_3)_2$ | $C_2H_5$ | H/H | 3-F,4-OH |
| $CH_2-CH_2-CH_2-CH_2$ | $COCH_3$ | H/H | 3-F, $4-OCH_3$ |
| $CH_2-CH_2-CH_2-CH_2$ | H | $CH_3$/H | $4-NHC_2H_5$ |

(Representative compound 2)

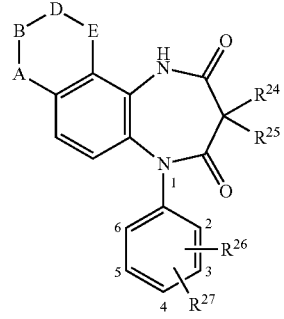

In the above-illustrated formula, A-B-D-E, $R^{24}/R^{25}$, $R^{26}$, and $R^{27}$ are shown in Tables 4 to 6.

TABLE 4

| A-B-D-E | $R^{24}/R^{25}$ | * | $R^{26}$ | $R^{27}$ |
|---|---|---|---|---|
| $CH_2-CH_2-CH_2-CH_2$ | H/H | 3 | 1H-tetrazol-5-yl | H |
| $C(CH_3)_2-CH_2-CH_2-CH_2$ | H/H | 3 | 1H-tetrazol-5-yl | H |
| $C(CH_3)_2-CH_2-CH_2-CH_2$ | H/H | 3 | 1H-tetrazol-1-yl | 4-F |
| $C(CH_3)_2CH_2CH_2C(CH_3)_2$ | H/H | 3 | 2-methyl-2H-tetrazol-5-yl | 3-F |
| $CH_2-CH_2-C(CH_3)_2-CH_2$ | H/H | 3 | 1,2,3-triazol-5-yl | 2-F |
| $CH_2-CH_2-CH_2-CH_2$ | H/H | 3 | 1,2,4-triazol-3-yl | H |
| $NH-CH_2-CH_2-CH_2$ | H/H | 3 | 5-trifluoromethyl-1,2,4-triazol-3-yl | H |
| $N(CH_3)-CH_2-CH_2-CH_2$ | H/H | 4 | 1H-imidazol-1-yl | H |
| $O-CH_2-CH_2-O$ | H/H | 4 | 1H-imidazol-2-yl | H |
| $O-CH_2-CH_2-O$ | H/H | 3 | 5-cyano-1H-1,2,3-triazol-4-yl | H |
| $C(CH_3)_2CH_2CH_2C(CH_3)_2$ | H/H | 3 | 1-methyl-1H-tetrazol-5-yl | H |
| $CH_2-CH_2-CH_2-CH_2$ | $CH_3$/H | 3 | pyrazol-3-yl | 4-OH |
| $CH_2-CH_2-CH_2-CH_2$ | $CH_3/CH_3$ | 3 | pyrazol-4-yl | H |

(Remark)
*: The position of $R^{26}$

TABLE 5

| A-B-D-E | $R^{24}/R^{25}$ | * | $R^{26}$ | $R^{27}$ |
|---|---|---|---|---|
| $C(CH_3)_2-CH_2-CH_2-CH_2$ | H/H | 3 | 5-oxo-1,2,4-oxadiazol-3-yl | 4-$NH_2$ |
| $CH_2-C(CH_3)_2-CH_2-CH_2$ | $CF_3$/H | 3 | 1,2,4-oxadiazol-3-yl | H |
| $CH_2-CH_2-C(CH_3)_2-CH_2$ | H/H | 3 | 1,3,4-oxadiazol-2-yl | 4-F |
| $CH_2-CH_2-CH_2-CH_2$ | H/H | 4 | pyrrole-1-yl | 3-F |
| $NH-CH_2-CH_2-CH_2$ | H/H | 4 | pyrrolidin-2-yl | H |
| $N(CH_3)-CH_2-CH_2-CH_2$ | H/H | 2 | 1,3-oxazol-5-yl | H |
| $O-CH_2-CH_2-O$ | H/H | 3 | 1,3-thiazol-5-yl | H |
| $O-CH_2-CH_2-O$ | H/H | 3 | 5-trifluoromethyl-1H-imidazol-2-yl | H |
| $C(CH_3)_2CH_2CH_2C(CH_3)_2$ | H/H | 3 | 5-chloro-1H-imidazol-2-yl | 4-OH |

(Remark)
*: The position of $R^{26}$

TABLE 6

| A-B-D-E | $R^{24}/R^{25}$ | * | $R^{26}$ | $R^{27}$ |
|---|---|---|---|---|
| $CH_2-CH_2-CH_2-CH_2$ | $CH_3$/H | 4 | 5-methyl-1H-imidazol-2-yl | 4-$NH_2$ |
| $CH_2-CH_2-CH_2-CH_2$ | $CH_3$/H | 4 | 5-amino-1H-imidazol-2-yl | 3-F |
| $CH_2-CH_2-CH_2-CH_2$ | $CH_3$/H | 3 | 2-ethyl-2H-tetrazol-5-yl | H |
| $C(CH_3)_2-CH_2-CH_2-CH_2$ | propyl/H | 3 | 2-(2,2,2-trifluoroethyl)-2H-tetrazol-5-yl | 2,6-F |
| $CH_2-C(CH_3)_2-CH_2-CH_2$ | H/H | 3 | 1,3-oxazol-2-yl | H |
| $CH_2-CH_2-C(CH_3)_2-CH_2$ | H/H | 3 | 1,3-thiazol-2-yl | H |
| $CH_2-CH_2-CH_2-CH_2$ | H/H | 4 | 3,5-dimethyl-isoxazol-4-yl | H |
| $NH-CH_2-CH_2-NH$ | H/H | 3 | 3-methyl-1,2,4-oxadiazol-5-yl | H |

(Remark)
*: The position of $R^{26}$

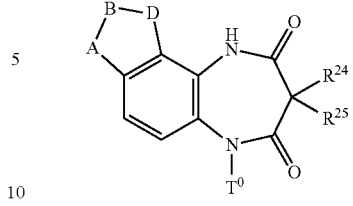

(Representative compound 3)

In the above-illustrated formula, A-B-D-E, $R^{24}/R^{25}$, and $T^0$ are shown in Tables 7 to 9.

TABLE 7

| A-B-D-E | $R^{24}/R^{25}$ | $T^0$ |
|---|---|---|
| $CH_2-CH_2-CH_2-CH_2$ | H/H | pyrimidin-2-yl |
| $C(CH_3)_2-CH_2-CH_2-CH_2$ | H/H | pyrimidin-5-yl |
| $CH_2-C(CH_3)_2-CH_2-CH_2$ | H/H | pyridin-2-yl |
| $CH_2-CH_2-C(CH_3)_2-CH_2$ | H/H | pyridin-3-yl |
| $CH_2-CH_2-CH_2-CH_2$ | H/H | pyridin-4-yl |
| $NH-CH_2-CH_2-CH_2$ | $CH_3$/H | thiophen-2-yl |
| $N(CH_3)-CH_2-CH_2-CH_2$ | H/H | thiophen-3-yl |
| $O-CH_2-CH_2-O$ | H/H | thiophen-3-yl |
| $O-CH_2-CH_2-O$ | H/H | 5-hydroxypyridin-3-yl |
| $C(CH_3)_2-CH_2-CH_2-C(CH_3)_2$ | H/H | 5-methoxypyridin-3-yl |
| $CH_2-CH_2-CH_2-CH_2$ | F/H | 5-aminopyridin-3-yl |
| $CH_2-CH_2-CH_2-CH_2$ | $CH_3/CH_3$ | 5-chloropyridin-3-yl |
| $CH_2-CH_2-CH_2-CH_2$ | Propyl/H | 6-chloropyridin-3-yl |

TABLE 8

| A-B-D-E | $R^{24}/R^{25}$ | $T^0$ |
|---|---|---|
| $CH_2-CH_2-CH_2-CH_2$ | Propyl/H | 6-chloropyridin-3-yl |
| $CH_2-CH_2-CH_2-CH_2$ | H/H | 1H-indazol-6-yl |
| $C(CH_3)_2-CH_2-CH_2-CH_2$ | H/H | 1H-indazol-5-yl |
| $CH_2-C(CH_3)_2-CH_2-CH_2$ | H/H | 1H-indazol-4-yl |
| $CH_2-CH_2-C(CH_3)_2-CH_2$ | H/H | 1H-benzotriazol-6-yl |
| $C(CH_3)_2-CH_2-CH_2-CH_2$ | H/H | 1H-benzotriazol-4-yl |
| $CH_2-CH_2-CH_2-CH_2$ | H/H | 1H-benzimidazol-6-yl |
| $CH_2-C(CH_3)_2-CH_2-CH_2$ | H/H | 1H-indazol-4-yl |
| $CH_2-CH_2-C(CH_3)_2-CH_2$ | H/H | 1H-indol-6-yl |
| $C(CH_3)_2-CH_2-CH_2-CH_2$ | H/H | 1H-indol-5-yl |
| $C(CH_3)_2-CH_2-CH_2-CH_2$ | H/H | 1H-indol-4-yl |
| $CH_2-C(CH_3)_2-CH_2-CH_2$ | H/H | benzisoxazol-6-yl |
| $C(CH_3)_2-CH_2-CH_2-CH_2$ | H/H | 1H-benzimidazol-5-yl |

TABLE 9

| A-B-D-E | $R^{24}/R^{25}$ | $T^0$ |
|---|---|---|
| $C(CH_3)_2-CH_2-CH_2-CH_2$ | H/H | 1H-benzimidazol-6-yl |
| $CH_2-C(CH_3)_2-CH_2-CH_2$ | H/H | 2-trifluoromethyl-1H-benzimidazol-5-yl |
| $CH_2-CH_2-CH_2-CH_2$ | H/H | quinolin-5-yl |
| $C(CH_3)_2-CH_2-CH_2-CH_2$ | H/H | quinolin-8-yl |

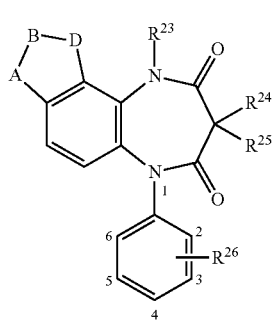

(Representative compound 4)

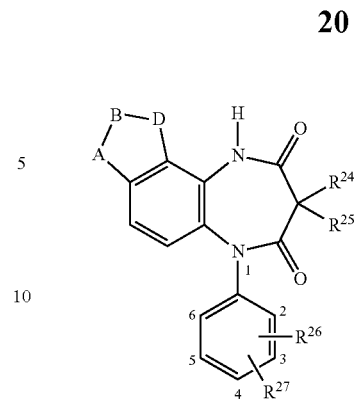

(Representative compound 5)

In the above-illustrated formula, A-B-D, $R^{23}$, $R^{24}/R^{25}$, and $R^{26}$ are shown in Tables 10 to 12.

In the above-illustrated formula, A-B-D, $R^{24}/R^{25}$, $R^{26}$, and $R^{27}$ are shown in Tables 13 to 15.

TABLE 10

| A-B-D | $R^{23}$ | $R^{24}/R^{25}$ | $R^{26}$ |
|---|---|---|---|
| $CH_2—CH_2—CH_2$ | H | H/H | 3-CN |
| $CH_2—CH_2—CH_2$ | H | H/H | 3-OH |
| $CH_2—CH_2—CH_2$ | H | H/H | $3-CO_2H$ |
| $CH_2—CH_2—CH_2$ | H | H/H | $3-CONH_2$ |
| $O—CH_2—O$ | H | H/H | $3,4-OCH_3$ |
| $O—CH_2—O$ | $CH_3$ | H/H | $3,4-OCH_3$ |
| $O—CH_2—O$ | $C_2H_5$ | H/H | 3-OH, 4-F |
| $O—CH_2—O$ | H | H/H | $3-NH_2$ |
| $CH_2—CH_2—CH_2$ | H | H/H | $3-NHCH_3$ |
| $CH_2—CH_2—CH_2$ | H | H/H | $3-CF_3$ |
| $CH_2—CH_2—CH_2$ | H | H/H | $3-NHCH_2CF_3$ |
| $CH_2—CH_2—CH_2$ | $CH_3$ | H/H | 2-OH, 3-OH |
| $O—CH_2—O$ | $C_2H_5$ | H/H | $3,4,5-CH_3$ |

TABLE 11

| A-B-D | $R^{23}$ | $R^{24}/R^{25}$ | $R^{26}$ |
|---|---|---|---|
| $O—CH_2—O$ | H | $CH_3$/H | 4-OH |
| $O—CH_2—O$ | H | $CH_3/CH_3$ | $4-NH_2$ |
| $O—CH_2—O$ | H | propyl/H | $4-NO_2$ |
| $CH_2—CH_2—CH_2$ | H | H/H | 4-CN |
| $CH_2—CH_2—CH_2$ | $CH_3$ | $CF_3$/H | 4-phenyl |
| $CH_2—CH_2—CH_2$ | $C_2H_5$ | H/H | $4-CH_2OH$ |
| $O—CH_2—O$ | H | H/H | $3-CH_2OH$ |
| $CH_2—CH_2—CH_2$ | H | H/H | $3-COCH_3$ |
| $CH_2—CH_2—CH_2$ | H | H/H | $3,5-OCH_3$ |
| $CH_2—CH_2—CH_2$ | H | H/H | 3-OH, $4-NH_2$ |
| $O—CH_2—O$ | $CH_3$ | H/H | $3-CH_2NH_2$ |
| $CH_2—CH_2—CH_2$ | $C_2H_5$ | H/H | $3-SO_2CH_3$ |
| $CH_2—CH_2—CH_2$ | H | $CH_3$/H | 3-isopropyl |
| $CH_2—CH_2—CH_2$ | H | $CH_3$/H | $3-N(CH_3)_2$ |
| $O—CH_2—O$ | H | $CH_3$/H | $4-COCH_3$ |
| $CH_2—CH_2—CH_2$ | H | propyl/H | $3,4-NH_2$ |

TABLE 12

| A-B-D | $R^{23}$ | $R^{24}/R^{25}$ | $R^{26}$ |
|---|---|---|---|
| $CH_2—CH_2—CH_2$ | H | H/H | $NHCH_3$ |
| $CH_2—CH_2—CH_2$ | $C_2H_5$ | H/H | $3-NHCH_2CF_3$ |
| $O—CH_2—O$ | H | H/H | $3-NHCOCH_3$ |
| $CH_2—CH_2—CH_2$ | H | H/H | $3-SO_2CH_3$ |
| $CH_2—CH_2—CH_2$ | H | H/H | $4-CH_3$ |
| $CH_2—CH_2—CH_2$ | H | H/H | 4-isopropyl |
| $O—CH_2—O$ | $CH_3$ | H/H | 3-phenyl |
| $CH_2—CH_2—CH_2$ | $C_2H_5$ | H/H | 3-F, 4-OH |
| $CH_2—CH_2—CH_2$ | $COCH_3$ | H/H | 3-F, $4-OCH_3$ |

TABLE 13

| A-B-D-E | $R^{24}/R^{25}$ | * | $R^{26}$ | $R^{27}$ |
|---|---|---|---|---|
| $CH_2—CH_2—CH_2$ | H/H | 3 | 1H-tetrazol-5-yl | H |
| $CH_2—CH_2—CH_2$ | H/H | 4 | 1H-tetrazol-5-yl | H |
| $CH_2—CH_2—CH_2$ | H/H | 3 | 1H-tetrazol-1-yl | 4-F |
| $CH_2—CH_2—CH_2$ | H/H | 3 | 2-methyl-2H-tetrazol-5-yl | H |
| $O—CH_2—O$ | H/H | 3 | 1,2,3-triazol-5-yl | 2-F |
| $O—CH_2—O$ | H/H | 3 | 1,2,4-triazol-3-yl | H |
| $O—CH_2—O$ | H/H | 3 | 5-trifluoromethyl-1,2,4-triazol-3-yl | H |
| $O—CH_2—O$ | H/H | 4 | 1H-imidazol-1-yl | H |
| $CH_2—CH_2—CH_2$ | H/H | 4 | 1H-imidazol-2-yl | H |
| $CH_2—CH_2—CH_2$ | H/H | 3 | 5-cyano-1H-1,2,3-triazol-4-yl | H |
| $CH_2—CH_2—CH_2$ | H/H | 3 | 1-methyl-1H-tetrazol-5-yl | H |
| $CH_2—CH_2—CH_2$ | $CH_3$/H | 3 | pyrazol-3-yl | 4-OH |

(Remark)
*: The position of $R^{26}$

TABLE 14

| A-B-D | $R^{24}/R^{25}$ | * | $R^{26}$ | $R^{27}$ |
|---|---|---|---|---|
| $O—CH_2—O$ | $CH_3/CH_3$ | 3 | pyrazol-4-yl | H |
| $O—CH_2—O$ | H/H | 3 | 5-oxo-1,2,4-oxadiazol-3-yl | $4-NH_2$ |
| $O—CH_2—O$ | $CF_3$/H | 3 | 1,2,4-oxadiazol-3-yl | H |
| $CH_2—CH_2—CH_2$ | H/H | 3 | 1,3,4-oxadiazol-2-yl | 4-F |
| $CH_2—CH_2—CH_2$ | H/H | 4 | pyrrole-1-yl | 3-F |
| $CH_2—CH_2—CH_2$ | H/H | 4 | pyrrolidin-2-yl | H |
| $O—CH_2—O$ | H/H | 2 | 1,3-oxazol-5-yl | H |
| $CH_2—CH_2—CH_2$ | H/H | 3 | 1,3-thiazol-5-yl | H |
| $CH_2—CH_2—CH_2$ | H/H | 3 | 5-trifluoromethyl-1H-imidazol-2-yl | H |
| $CH_2—CH_2—CH_2$ | H/H | 3 | 5-chloro-1H-imidazol-2-yl | 4-OH |
| $O—CH_2—O$ | $CH_3$/H | 4 | 5-methyl-1H-imidazol-2-yl | $4-NH_2$ |
| $CH_2—CH_2—CH_2$ | $CH_3$/H | 4 | 5-amino-1H-imidazol-2-yl | 3-F |

(Remark)
*: The position of $R^{26}$

TABLE 15

| A-B-D | $R^{24}/R^{25}$ | * | $R^{26}$ | $R^{27}$ |
|---|---|---|---|---|
| $CH_2—CH_2—CH_2$ | $CH_3$/H | 3 | 2-ethyl-2H-tetrazol-5-yl | H |
| $CH_2—CH_2—CH_2$ | propyl/H | 3 | 2-(2,2,2-trifluoroethyl)-2H-tetrazol-5-yl | 2,6-F |
| $O—CH_2—O$ | H/H | 3 | 1,3-oxazol-2-yl | H |
| $CH_2—CH_2—CH_2$ | H/H | 3 | 1,3-thiazol-2-yl | H |
| $CH_2—CH_2—CH_2$ | H/H | 4 | 3,5-dimethylisoxazol-4-yl | H |
| $CH_2—CH_2—CH_2$ | H/H | 3 | 3-methyl-1,2,4-oxadiazol-5-yl | H |

(Remark)
*: The position of $R^{26}$

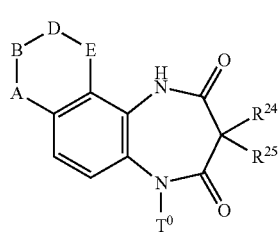

(Representative compound 6)

In the above-illustrated formula, A-B-D, $R^{24}/R^{25}$, and $T^0$ are shown in Tables 16 to 18.

TABLE 16

| A-B-D | $R^{24}/R^{25}$ | $T^0$ |
|---|---|---|
| CH$_2$—CH$_2$—CH$_2$ | H/H | pyrimidin-2-yl |
| CH$_2$—CH$_2$—CH$_2$ | H/H | pyrimidin-5-yl |
| CH$_2$—CH$_2$—CH$_2$ | H/H | pyridin-2-yl |
| CH$_2$—CH$_2$—CH$_2$ | H/H | quinolin-2-yl |
| CH$_2$—CH$_2$—CH$_2$ | H/H | quinolin-3-yl |
| CH$_2$—CH$_2$—CH$_2$ | H/H | pyridin-3-yl |
| O—CH$_2$—O | H/H | pyridin-4-yl |
| O—CH$_2$—O | CH$_3$/H | thiophen-2-yl |
| O—CH$_2$—O | H/H | thiophen-3-yl |
| O—CH$_2$—O | H/H | thiophen-3-yl |
| CH$_2$—CH$_2$—CH$_2$ | H/H | 5-hydroxypyridin-3-yl |
| CH$_2$—CH$_2$—CH$_2$ | H/H | 5-methoxypyridin-3-yl |
| NH—CH$_2$—CH$_2$ | F/H | 5-aminopyridin-3-yl |

TABLE 17

| A-B-D-E | $R^{24}/R^{25}$ | $T^0$ |
|---|---|---|
| CH$_2$—CH$_2$—CH$_2$ | CH$_3$/CH$_3$ | 5-chloropyridin-3-yl |
| O—CH$_2$—O | propyl/H | 6-chloropyridin-3-yl |
| O—CH$_2$—O | propyl/H | 6-chloropyridin-3-yl |
| O—CH$_2$—O | H/H | 1H-indazol-6-yl |
| O—CH$_2$—O | H/H | 1H-indazol-5-yl |
| CH$_2$—CH$_2$—CH$_2$ | H/H | 1H-indazol-4-yl |
| CH$_2$—CH$_2$—CH$_2$ | H/H | 1H-benzotriazol-6-yl |
| CH$_2$—CH$_2$—CH$_2$ | H/H | 1H-benzotriazol-4-yl |
| O—CH$_2$—O | H/H | 1H-benzimidazol-6-yl |
| CH$_2$—CH$_2$—CH$_2$ | H/H | 1H-indazol-4-yl |
| CH$_2$—CH$_2$—CH$_2$ | H/H | 1H-indol-6-yl |

TABLE 18

| A-B-D-E | $R^{24}/R^{25}$ | $T^0$ |
|---|---|---|
| NH—CH$_2$—CH$_2$ | H/H | 1H-indol-5-yl |
| O—CH$_2$—O | H/H | 1H-indol-4-yl |
| CH$_2$—CH$_2$—CH$_2$ | H/H | benzisoxazol-6-yl |
| CH$_2$—CH$_2$—CH$_2$ | H/H | 1H-benzimidazol-5-yl |
| CH$_2$—CH$_2$—CH$_2$ | H/H | 1H-benzimidazol-6-yl |
| O—CH$_2$—O | H/H | 2-trifluoromethyl-1H-benzimidazol-5-yl |
| CH$_2$—CH$_2$—CH$_2$ | H/H | quinolin-5-yl |
| CH$_2$—CH$_2$—CH$_2$ | H/H | quinolin-8-yl |

The pharmacological effects of the present invention are described below.

P2X$_4$ antagonism of the compound of the present invention is measured as described below.

1321N1 cells stably expressing human P2X$_4$ receptors were adopted for calcium influx assay. P2X$_4$/1321N1 cells were plated in 96-well assay plate and cultured for 24 hours in an atmosphere of 5% CO$_2$ at 37° C. Fura-2 AM calcium indicator dissolved in an extracellular solution for calcium imaging was loaded onto cells for 45 minutes at room temperature. The fluorescence was detected by FLUOstar OPTIMA micro plate reader (BMG labtech). The cells were alternatively illuminated with two excitations wavelengths (340 nm and 380 nm) via xenon lamp and the emitted fluorescence was measured at 510 nm. The fluorescence changes after the treatment of 1 μM ATP were monitored and determined the fluorescence ratio ($F_{340}/F_{380}$) as the index of intracellular calcium change. Tested compounds were treated to cells 15 min before the addition of ATP and the inhibition activities of compounds were calculated by comparing the Ca$^{2+}$ response with control in the absence of tested compound.

As is evident from the below-described results shown in Examples 19 and 20, the compound of the present invention shows excellent P2X$_4$ receptor antagonism.

Therefore, it is considered that the diazepine derivative represented by the formula (I), (II), (III), or its pharmacologically acceptable salt, which shows P2X$_4$ receptor antagonism, is effective as an agent for prevention or treatment of nociceptive, inflammatory, and neuropathic pains. In more detail, it is effective as a preventive or therapeutic agent for pains caused by various cancers, diabetic neuritis, viral diseases such as herpes, and osteoarthritis. The preventive or therapeutic agent of the present invention can also be used in combination with other agents such as opioid analgesic (e.g., morphine, fentanyl), sodium channel inhibitor (e.g., novocaine, lidocaine), or NSAIDs (e.g., aspirin, ibuprofen). The agent for pains caused by cancers can be used in combination with a carcinostatic such as a chemotherapic.

The compound of the present invention can be administered to human beings by ordinary administration methods such as oral administration or parenteral administration.

The compound can be granulated in ordinary manners for the preparation of pharmaceuticals. For instance, the compound can be processed to give pellets, granule, powder, capsule, suspension, injection, suppository, and the like.

Ordinary additives such as vehicles, disintegrators, binders, lubricants, dyes, and diluents are used for the preparation of these pharmaceuticals. As the vehicles, lactose, D-mannitol, crystalline cellulose, and glucose can be mentioned. Further, there can be mentioned starch and carboxymethylcellulose calcium (CMC-Ca) as the disintegrators, magnesium stearate and talc as the lubricants, and hydroxypropylcellulose (HPC), gelatin and polyvinylpirrolidone (PVP) as the binders. The preparation of an injection can be made using solvents, stabilizers, dissolution-aids, suspensions, emulsifiers, soothing agents, buffers, or preservatives.

The compound of the invention can be administered to an adult generally in an amount of approx. 0.01 mg to 100 mg a day by parenteral administration and 1 mg to 2,000 mg a day by oral administration. The dosage can be adjusted in consideration of age and conditions of the patient.

The present invention is further described by the following non-limiting examples.

EXAMPLES

Example 1

5-(3-Cyanophenyl)-8,9,10,11-tetrahydronaphtho[2,1-b][1,4]diazepine-2,4(3H,5H)-dione (1) 3-(1-Nitro-5,6,7,8-tetrahydronaphthalen-2-ylamino)benzonitrile An anhydrous toluene (30 mL) suspension of 1-nitro-5,6,7,8-tetrahydronaphthalen-2-yl triflate (1.95 g, 6.00 mmol), 3-aminobenzonitrile (1.06 g, 9.00 mmol), potassium carbonate (830 mg, 6.00 mmol), tetrakis(triphenylphosphine)palladium (346 mg, 0.30 mmol), and triphenylphosphine (158 mg, 0.60 mmol) was stirred at 110° C. for 18 hours. The reaction mixture was cooled on standing, and filtered. The filtrate was diluted with ethyl acetate. The obtained organic solution was washed with purified water, and dried over anhydrous sodium sulfate. The solvent was removed by evaporation under reduced pressure. The residue was purified by silica gel column chromatography (chloroform) to give the titled compound as orange powder (1.515 g, yield 86%).

$^1$H NMR (CDCl$_3$, 400 MHz) δ: 1.7-1.9 (4H, m), 2.7-2.8 (4H, m), 6.90 (1H, br s), 7.1-7.4 (6H, m)

(2) 3-(1-Amino-5,6,7,8-tetrahydronaphthalen-2-ylamino)benzonitrile

To a methanol (10 mL) and anhydrous tetrahydrofuran (30 mL) solution of 3-(1-nitro-5,6,7,8-tetrahydronaphthalen-2-ylamino)benzonitrile (1.52 g, 5.17 mmol was added platinum oxide (50 mg), and the mixture was hydrogenated for 29 hours at room temperature under atmospheric pressure. After removal of the catalyst by filtration, the solvent was removed by evaporation under reduced pressure. The residue was purified by silica gel column chromatography (chloroform) to give the titled compound as yellow powder (747 mg, yield 55%).

$^1$H NMR (CDCl$_3$, 400 MHz) δ: 1.7-1.9 (4H, m), 2.50 (2H, t, J=6 Hz), 2.76 (2H, t, J=6 Hz), 3.77 (2H, br s), 5.26 (1H, br s), 6.54 (1H, d, J=8 Hz), 6.8-6.9 (3H, m), 7.02 (1H, d, J=7 Hz), 7.23 (1H, t, J=8 Hz)

(3) 5-(3-Cyanophenyl)-8,9,10,11-tetrahydronaphtho[2,1-b][1,4]diazepine-2,4(3H,5H)-dione To an anhydrous tetrahydrofuran (30 mL) solution of 3-(1-amino-5,6,7,8-tetrahydronaphthalen-2-ylamino)benzonitrile (747 mg, 2.84 mmol) was added an anhydrous tetrahydrofuran (5 mL) solution of malonyl chloride (276 μL, 2.84 mmol) under cooling in ice-bath. The mixture was stirred for 30 minutes under cooling in ice-bath, and for 2 hours at room temperature. To the mixture was added purified water. The mixture was extracted with ethyl acetate, washed with purified water, and dried over anhydrous sodium sulfate. The solvent was removed by evaporation under reduced pressure. The residue was purified by silica gel chromatography (hexane/ethyl acetate=1/1) to give the titled compound as white powder (333 mg, yield 35%).

$^1$H NMR (CDCl$_3$, 400 MHz) δ: 1.7-2.1 (4H, m), 2.6-2.9 (4H, m), 3.49 (1H, d, =12 Hz), 3.54 (1H, d, J=12 Hz), 6.62 (1H, J=8 Hz), 6.88 (1H, d, J=8 Hz), 7.4-7.6 (4H, m), 7.67 (1H, br s)

Example 2

5-[3-(1H-Tetrazol-5-yl)phenyl]-8,9,10,11-tetrahydronaphtho[2,1-b][1,4]diazepine-2,4(3H,5H)-dione sodium salt

(1) 5-[3-(1H-Tetrazol-5-yl)phenyl]-8,9,10,11-tetrahydronaphtho[2,1-b][1,4]diazepine-2,4(3H,5H)-dione To an anhydrous DMF (5 mL) solution of 5-(3-cyanophenyl)-8,9,10,11-tetrahydronaphtho[2,1-b][1,4]diazepine-2,4(3H,5H)-dione (302 mg, 0.91 mmol) was added tri-n-butyltin azide (499 μL, 1.82 mmol). The mixture was stirred at 110° C. for 24 hours. The reaction mixture was cooled on standing, poured into saturated aqueous sodium hydrogen carbonate solution, and washed with ethyl acetate. After neutralization of the aqueous layer by addition of 1M hydrochloric acid, the layer was extracted with ethyl acetate, washed with purified water, and dried over anhydrous sodium sulfate. The solvent was removed by evaporation under reduced pressure. The residue was purified by chromatography (chloroform/methanol=95/5) to give the titled compound as slightly yellow powder (242 mg, yield 71%).

$^1$H NMR (CD$_3$OD, 400 MHz) δ: 1.7-2.0 (4H, m), 2.7-3.0 (4H, m), 3.28 (1H, d, J=12 Hz), 3.68 (1H, d, J=12 Hz), 6.76 (1H, d, J=8 Hz), 6.93 (1H, d, J=8 Hz), 7.44 (1H, d, J=8 Hz), 7.64 (1H, t, J=8 Hz), 7.88 (1H, s), 8.00 (1H, d, J=8 Hz)

(2) 5-[3-(1H-Tetrazol-5-yl)phenyl]-8,9,10,11-tetrahydronaphtho[2,1-b][1,4]diazepine-2,4(3H,5H)-dione sodium salt To a methanol (2 mL) and purified water (1 mL) solution of 5-[3-(1H-tetrazol-5-yl)phenyl]-8,9,10,11-tetrahydronaphtho[2,1-b][1,4]diazepine-2,4(3H,5H)-dione (85 mg, 0.23 mmol) was added 1M aqueous sodium hydrogen carbonate solution (227 μL). The mixture was stirred at room temperature for 25 minutes. After concentrating the mixture under reduced pressure, the residue was washed with ether, and dried to solidify under reduced pressure to give the titled compound as pale yellow powder (86 mg, yield 96%).

$^1$H NMR (CD$_3$OD, 400 MHz) δ: 1.7-2.0 (4H, m), 2.7-3.0 (4H, m), 3.35 (2H, s), 6.79 (1H, d, J=9 Hz), 6.91 (1H, d, J=9 Hz), 7.31 (1H, d, J=8 Hz), 7.52 (1H, t, J=8 Hz), 7.82 (1H, s), 8.02 (1H, d, J=8 Hz)

IR (cm$^{-1}$, KBr): 3415, 2933, 1689, 1466, 1421, 1387, 1313, 984, 793, 760, 696.

Example 3

5-(3-Hydroxyphenyl)-8,9,10,11-tetrahydronaphtho[2,1-b][1,4]diazepine-2,4(3H,5H)-dione

(1) N$^2$-(3-Benzyloxyphenyl)-5,6,7,8-tetrahydronaphthalene-1,2-diamine

An anhydrous toluene (30 mL) suspension of 1-nitro-5,6,7,8-tetrahydronaphthalen-2-yl triflate (1.95 g, 6.00 mmol), 3-benzyloxyaniline (1.43 g, 7.20 mmol), potassium carbonate (0.83 g, 6.00 mmol), tetrakis(triphenylphosphine)palladium (0.35 g, 0.30 mmol), and triphenylphosphine (0.16 g, 0.60 mmol) was stirred at 110° C. for 16 hours. After cooling the mixture on standing, ethyl acetate and water were added to the mixture. Insoluble was removed by filtration. The organic layer was washed with saturated brine, and dried over anhydrous sodium sulfate. The solvent was removed by evaporation under reduced pressure. The residue was subjected to silica gel column chromatography (ethyl acetate/hexane=1/5) to give red oil (0.81 g).

The obtained crude 3-benzyloxy-N-(1-nitro-5,6,7,8-tetrahydronaphthalen-2-yl)aniline (0.81 g) was dissolved in tetrahydrofuran (10 mL)-ethanol (10 mL). To the solution was added concentrated hydrochloric acid (2 mL). To the mixture was added tin(II) chloride dihydrate (2.19 g, 9.72 mmol) over 5 minutes while stirring in ice-bath. The mixture was stirred at room temperature for 17 hours and at 50° C. for 4 hours. To the reaction mixture was added 2M aqueous sodium hydroxide solution (25 mL) while stirring in ice-bath. The mixture was extracted with ethyl acetate, washed with water and with saturated brine, and dried over anhydrous sodium sulfate. The solvent was removed by evaporation under reduced pressure to give red oil (0.81 g). The oil was purified by silica gel column chromatography (ethyl acetate/hexane=1/4) to give the titled compound as slightly yellow crystal (80 mg, yield 4%).

$^1$H NMR (CDCl$_3$, 400 MHz) δ: 1.7-1.9 (4H, m), 2.49 (2H, t, J=7 Hz), 2.74 (2H, t, J=7 Hz), 3.77 (2H, br s), 4.99 (2H, s), 5.07 (1H, br s), 6.2-6.3 (2H, m), 6.41 (1H, dd, J=2 Hz, 8 Hz), 6.51 (1H, d, J=8 Hz), 6.89 (1H, d, J=8 Hz), 7.09 (1H, t, J=8 Hz), 7.2-7.4 (5H, m).

(2) 5-(3-Benzyloxyphenyl)-8,9,10,11-tetrahydronaphtho[2,1-b][1,4]diazepine-2,4(3H,5H)-dione To an anhydrous tetrahydrofuran (15 mL) solution of N$^2$-(3-benzyloxyphenyl)-5,6,7,8-tetrahydronaphthalene-1,2-diamine (151 mg, 0.44 mmol) was added malonyl chloride (50 µL, 0.53 mmol) while stirring in ice-bath. The mixture was stirred at room temperature for 3 hours. To the mixture was added methanol (5 mL) while stirring in ice-bath. The mixture was stirred under cooling in ice-bath for 1 hour, and at room temperature for 1 hour. The solvent was removed by evaporation under reduced pressure. The residue was purified by silica gel column chromatography (ethyl acetate/hexane=1/1) to give the titled compound as yellow oil (58 mg, yield 32%).

$^1$H NMR (CDCl$_3$, 400 MHz) δ: 1.5-2.1 (4H, m), 2.6-2.9 (4H, m), 3.4-3.6 (2H, m), 4.99 (2H, s), 6.69 (1H, d, J=8 Hz), 6.8-7.0 (4H, m), 7.2-7.4 (6H, m).

(3) 5-(3-Hydroxyphenyl)-8,9,10,11-tetrahydronaphtho[2,1-b][1,4]diazepine-2,4(3H,5H)-dione 5-(3-Benzyloxyphenyl)-8,9,10,11-tetrahydronaphtho[2,1-b][1,4]diazepine-2,4(3H,5H)-dione (58 mg, 0.14 mmol) was dissolved in tetrahydrofuran (3 mL)-methanol (3 mL). To the solution was added 10% palladium-carbon (6 mg). The mixture was stirred under hydrogen atmosphere at room temperature for 6 hours. Insoluble was removed by filtration. The filtrate was concentrated under reduced pressure. The residue was purified by silica gel column chromatography (chloroform/methanol=50/1) to give the titled compound as slightly yellow crystal (30 mg, yield 66%).

$^1$H NMR (DMSO-d$_6$, 400 MHz) δ: 1.6-1.9 (4H, m), 2.5-2.6 (1H, m), 2.6-2.8 (2H, m), 2.8-3.0 (1H, m), 3.01 (1H, d, J=12 Hz), 3.54 (1H, d, J=12 Hz), 6.5-6.6 (2H, m), 6.66 (1H, d, J=8 Hz), 6.70 (1H, dd, J=2 Hz, 8 Hz), 6.88 (1H, d, J=8 Hz), 7.19 (1H, t, J=8 Hz), 9.59 (1H, br s), 9.86 (1H, s).

Example 4

5-(3-Cyanophenyl)-5,8,9,10-tetrahydroindeno[5,4-b][1,4]diazepine-2,4(1H,3H)-dione (1) 4-Nitroindan-5-yl triflate 5-Indanol (13.4 g, 100 mmol) was dissolved in acetic acid (100 mL). To the solution was dropwise added fuming nitric acid (4.1 mL) over 10 minutes while stirring in ice-bath. The mixture was stirred under cooling in ice-bath for 30 minutes. The reaction mixture was poured into ice-cold water (270 mL), and extracted with ethyl acetate. The ethyl acetate layer was washed with saturated brine, and dried over anhydrous sodium sulfate. The solvent was removed by evaporation under reduced pressure. The residue was purified by silica gel column chromatography (ethyl acetate/hexane=1/10) to give yellow oil (12.5 g).

The obtained mixture of 4-nitro-5-indanol and 6-nitro-5-indanol (11.9 g, 66.4 mmol) was dissolved in dry dichloromethane (60 mL). To the solution was added triethylamine (10.2 mL, 73.0 mmol). To the solution was dropwise added trifluoromethanesulfonic anhydride (10.9 mL, 66.4 mmol) over 70 minutes while stirring in ice-bath. The mixture was stirred at room temperature for 3 hours. The solvent was removed by evaporation under reduced pressure. To the residue were added ice-cold water and 2M hydrochloric acid (4 mL). The mixture was extracted with ethyl acetate. The ethyl acetate layer was washed with saturated brine, and dried over anhydrous sodium sulfate. The solvent was removed by evaporation under reduced pressure. The residue was purified by silica gel column chromatography (toluene/hexane=1/2-1/1) to give the titled compound as pale yellow crystal (7.0 g, yield 24%) and 6-nitroindan-5-yl triflate (12.0 g, yield 41%) as slightly yellow oil.

$^1$H NMR (CDCl$_3$, 400 MHz) δ: 2.1-2.3 (2H, m), 3.04 (2H, t, J=8 Hz), 3.21 (2H, t, =8 Hz), 7.22 (1H, d, J=8 Hz), 7.46 (1H, d, J=8 Hz).

(2) 3-(4-Nitroindan-5-yl)aminobenzonitrile

A dry toluene (50 mL) suspension of 4-nitroindan-5-yl triflate (3.11 g, 10.0 mmol), 3-aminobenzonitrile (1.77 g, 15.0 mmol), potassium carbonate (1.38 g, 10.0 mmol), tetrakis(triphenylphosphine)palladium (0.57 g, 0.50 mmol), and triphenylphosphine (0.26 g, 1.00 mmol) was refluxed for 66 hours. After cooling on standing, insoluble was removed by filtration. The filtrate was concentrated under reduced pressure. The residue was purified by silica gel column chromatography (ethyl acetate/hexane=1/5) to give the titled compound as orange crystal (0.84 g, yield 30%).

$^1$H NMR (CDCl$_3$, 400 MHz) δ: 2.1-2.2 (2H, m), 2.93 (2H, t, J=8 Hz), 3.31 (2H, t, J=7 Hz), 7.17 (1H, d, J=8 Hz), 7.3-7.5 (5H, m), 8.64 (1H, s).

(3) 3-(4-Aminoindan-5-yl)aminobenzonitrile 3-(4-Nitroindan-5-ylamino)benzonitrile (0.84 g, 3.00 mmol) was dissolved in tetrahydrofuran (84 mL)-methanol (21 mL). To the solution was added water-containing 5% palladium-carbon (0.08 g). The mixture was stirred under hydrogen atmosphere at room temperature for 16 hours. Insoluble was removed by filtration. The filtrate was concentrated under reduced pressure to give the titled compound as yellowish brown crystal (0.75 g, yield 100%).

$^1$H NMR (CDCl$_3$, 400 MHz) δ: 2.1-2.2 (2H, m), 2.77 (2H, t, J=7 Hz), 2.94 (2H, t, J=8 Hz), 3.70 (2H, br s), 4.99 (2H, s), 5.28 (1H, br s), 6.67 (1H, d, J=8 Hz), 6.8-6.9 (3H, m), 7.02 (1H, d, J=8 Hz), 7.22 (1H, d, J=8 Hz).

(4) 5-(3-Cyanophenyl)-5,8,9,10-tetrahydroindeno[5,4-b][1,4]diazepine-2,4(1H,3H)-dione To a dry tetrahydrofuran (75 mL) solution of 3-(4-aminoindan-5-ylamino)benzonitrile (0.75 g, 3.00 mmol) was added malonyl chloride (0.35 mL, 3.60 mmol) while stirring in ice-bath. The mixture was stirred under cooling in ice-bath for 1 hour and at room temperature for 1 hour. To the mixture was added methanol (5 mL) while stirring in ice-bath. The mixture was stirred under cooling in ice-bath for 1 hour and at room temperature for 1 hour. To the reaction mixture was added methanol (25 mL) while stirring in ice-bath. The mixture was stirred under cooling in ice-bath for 1 hour and at room temperature for 1 hour. The solvent was removed by evaporation under reduced pressure. The residue was purified by silica gel column chromatography (ethyl acetate/hexane=2/1-4/1) to slightly yellow crystal (0.40 g). The crystal was recrystallized from ethyl acetate to give the titled compound as white crystal (0.28 g, yield 29%).

Melting point 250-251° C.

$^1$H NMR (DMSO-d$_6$, 400 MHz) δ: 2.0-2.1 (2H, m), 2.7-3.0 (3H, m), 3.09 (1H, d, J=12 Hz), 3.1-3.3 (1H, m), 3.63 (1H, d, J=12 Hz), 6.63 (1H, d, J=8 Hz), 7.00 (1H, d, J=8 Hz), 7.45 (1H, d, J=8 Hz), 7.62 (1H, t, J=8 Hz), 7.7-7.8 (2H, m), 10.24 (1H, s).

Example 5

5-[3-(1H-Tetrazol-5-yl)phenyl]-5,8,9,10-tetrahydroindeno[5,4-b][1,4]diazepine-2,4(1H,3H)-dione sodium salt (1) 5-[3-(1H-Tetrazol-5-yl)phenyl]-5,8,9,10-tetrahydro-1H-indeno[5,4-b][1,4]diazepine-2,4(1H,3H)-dione 5-(3-Cyanophenyl)-5,8,9,10-tetrahydroindeno[5,4-b][1,4]diazepine-2,4(3H,5H)-dione (159 mg, 0.50 mmol) was mixed with tri-n-butyltin azide (332 mg, 1.00 mmol), toluene (8 mL) and dimethylformamide (2 mL). The mixture was refluxed for 24 hours. After cooling on standing, to the mixture was added 2M hydrochloric acid (2.5 mL), and the mixture was stirred at room temperature for 2 hours. The mixture was extracted with ethyl acetate, washed with saturated brine, and dried over anhydrous sodium sulfate. The solvent was removed by evaporation under reduced pressure. The residue was purified by silica gel column chromatography (chloroform/methanol=50/1) to give slightly yellow crystal. The crystal was recrystallized from acetone-hexane to give the titled compound as slightly yellow crystal (90 mg, yield 50%).

$^1$H NMR (CDCl$_3$, 400 MHz) δ: 2.1-2.4 (2H, m), 2.9-3.1 (3H, m), 3.2-3.3 (1H, m), 3.59 (1H, d, J=11 Hz), 3.66 (1H, d, J=11 Hz), 6.52 (1H, d, J=8 Hz), 6.67 (1H, s), 6.94 (1H, d, J=8 Hz), 7.12 (1H, t, J=8 Hz), 7.52 (1H, d, J=8 Hz), 7.83 (1H, d, J=8 Hz), 9.67 (1H, br s).

(2) 5-[3-(1H-Tetrazol-5-yl)phenyl]-5,8,9,10-tetrahydroindeno[5,4-b][1,4]diazepine-2,4(1H,3H)-dione sodium salt 5-[3-(1H-Tetrazol-5-yl)phenyl]-5,8,9,10-tetrahydroindeno[5,4-b][1,4]diazepine-2,4(1H,3H)-dione (90 mg, 0.25 mmol) was dissolved in ethanol (45 mL). To the solution was added a solution of sodium hydrogencarbonate (21 mg, 0.25 mmol) in water (4 mL). The solvent was removed by evaporation under reduced pressure to give the titled compound as a pale brown amorphous form (97 mg, yield 100%).

$^1$H NMR (DMSO-d$_6$, 400 MHz) δ: 2.0-2.1 (2H, m), 2.7-3.0 (3H, m), 3.09 (1H, d, J=12 Hz), 3.1-3.3 (1H, m), 3.64 (1H, d, J=12 Hz), 6.72 (1H, d, J=8 Hz), 6.98 (1H, d, J=8 Hz), 7.16 (1H, d, J=8 Hz), 7.44 (1H, t, J=8 Hz), 7.61 (1H, s), 7.91 (1H, d, J=7 Hz), 10.21 (1H, s).

Example 6

5-[3-(2-Methyl-2H-tetrazol-5-yl)phenyl]-5,8,9,10-tetrahydroindeno[5,4-b][1,4]diazepine-2,4(1H,3H)-dione and 5-[3-(1-methyl-1H-tetrazol-5-yl)phenyl]-5,8,9,10-tetrahydroindeno[5,4-b][1,4]diazepine-2,4(1H,3H)-dione 5-[3-(1H-Tetrazol-5-yl)phenyl]-5,8,9,10-tetrahydroindeno[5,4-b][1,4]diazepine-2,4(1H,3H)-dione sodium salt (46 mg, 0.12 mmol) was dissolved in dry dimethylsulfoxide (2 mL). To the solution was added methyl iodide (37 μL, 0.60 mmol). The mixture was stirred at room temperature for 72 hours. To the mixture was added water. The mixture was extracted with ethyl acetate, washed with saturated brine, and dried over anhydrous sodium sulfate. The solvent was removed by evaporation under reduced pressure. The residue was purified by silica gel column chromatography (ethyl acetate/hexane=2/1-3/1) to give 5-[3-(2-methyl-2H-tetrazol-5-yl)phenyl]-5,8,9,10-tetrahydroindeno[5,4-b][1,4]diazepine-2,4(1H,3H)-dione (17 mg, yield 38%) and 5-[3-(1-methyl-1H-tetrazol-5-yl)phenyl]-5,8,9,10-tetrahydroindeno[5,4-b][1,4]diazepine-2,4(1H,3H)-dione (5 mg, yield 11%).

$^1$H NMR (DMSO-d$_6$, 400 MHz)

5-[3-(2-Methyl-2H-tetrazol-5-yl)phenyl]-5,8,9,10-tetrahydroindeno[5,4-b][1,4]diazepine-2,4(1H,3H)-dione δ: 2.0-2.1 (2H, m), 2.7-3.0 (3H, m), 3.10 (1H, d, J=12 Hz), 3.1-3.3 (1H, m), 3.66 (1H, d, J=12 Hz), 4.41 (3H, s), 6.70 (1H, d, J=8 Hz), 7.00 (1H, d, J=8 Hz), 7.38 (1H, d, J=8 Hz), 7.63 (1H, t, J=8 Hz), 7.77 (1H, s), 8.00 (1H, d, J=7 Hz), 10.22 (1H, s).

5-[3-(1-Methyl-1H-tetrazol-5-yl)phenyl]-5,8,9,10-tetrahydroindeno[5,4-b][1,4]diazepine-2,4(1H,3H)-dione δ: 2.0-2.1 (2H, m), 2.7-3.0 (3H, m), 3.10 (1H, d, J=12 Hz), 3.1-3.3 (1H, m), 3.65 (1H, d, J=12 Hz), 4.16 (3H, s), 6.72 (1H, d, J=8 Hz), 7.01 (1H, d, J=8 Hz), 7.39 (1H, d, J=8 Hz), 7.67 (1H, t, J=8 Hz), 7.73 (1H, s), 7.80 (1H, d, J=8 Hz), 10.23 (1H, s).

Example 7

5-(3-tert-Butoxycarbonylaminophenyl)-1,5,8,9,10,11-hexahydronaphtho[1,2-b][1,4]diazepine-2,4-dione (1) tert-Butyl 3-(1-nitro-5,6,7,8-tetrahydronaphthalen-2-ylamino)phenyl]carbamate 1-Nitro-5,6,7,8-tetrahydronaphthalen-2-yl triflate (2.00 g, 6.15 mmol) and tert-butyl(3-aminophenyl)carbamate (1.28 g, 6.15 mmol) were used in a process similar to Example 1 (1) to give the titled compound as red oil (1.51 g, yield 64%).

$^1$H NMR (CDCl$_3$, 400 MHz) δ: 1.51 (9H, s), 1.7-1.8 (4H, m), 2.7-2.8 (4H, m), 6.75 (1H, dd, J=2 Hz, 8 Hz), 6.89 (1H, dd, J=2 Hz, 8 Hz), 7.0-7.1 (2H, m), 7.1-7.2 (2H, m), 7.24 (1H, br s).

(2) tert-Butyl 3-(1-amino-5,6,7,8-tetrahydronaphthalen-2-ylamino)phenyl]carbamate tert-Butyl 3-(1-nitro-5,6,7,8-tetrahydronaphthalen-2-ylamino)phenyl]carbamate (1.50 g, 3.91 mmol) and 10% palladium-carbon (0.15 g) were used in a process similar to Example 1(2) to give the titled compound as white crystal (0.78 g, yield 57%).

$^1$H NMR (CDCl$_3$, 400 MHz) δ: 1.49 (9H, s), 1.7-2.0 (4H, m), 2.49 (2H, t, J=6 Hz), 2.74 (2H, t, J=6 Hz), 3.80 (2H, br s), 5.08 (1H, br s), 6.3-6.4 (2H, m), 6.52 (1H, d, J=8 Hz), 6.89 (1H, d, J=8 Hz), 7.06 (1H, t, J=8 Hz).

(3) 5-(3-tert-Butoxycarbonylaminophenyl)-1,5,8,9,10,11-hexahydronaphtho[1,2-b][1,4]diazepine-2,4-dione tert-Butyl 3-(1-amino-5,6,7,8-tetrahydronaphthalen-2-ylamino)phenyl]carbamate (353 mg, 1.0 mmol) was used in a process similar to Example 1(3) to give the titled compound as a yellow amorphous substance (220 mg, yield 52%).

$^1$H NMR (CDCl$_3$, 400 MHz) δ: 1.48 (9H, s), 1.7-2.1 (4H, m), 2.6-2.8 (4H, m), 3.4-3.5 (2H, m), 6.71 (1H, d, J=8 Hz), 6.7-6.9 (3H, m), 7.2-7.4 (3H, m), 8.21 (1H, br s).

Example 8

5-(3-Aminophenyl)-1,5,8,9,10,11-hexahydronaphtho[1,2-b][1,4]diazepine-2,4-dione hydrochloride 5-(3-tert-Butoxycarbonylaminophenyl)-1,5,8,9,10,11-hexahydronaphtho[1,2-b][1,4]diazepine-2,4-dione (180 mg, 0.43 mmol) obtained in Example 7(3) was suspended in dichloromethane (15 mL). To the suspension was dropwise added a mixed solution of trifluoroacetic acid (3 mL)-dichloromethane (3 mL) while stirring in ice-bath. The mixture was stirred under cooling in ice-bath for 1 hour and at room temperature for 1 hour. To the mixture were added potassium carbonate and a small amount of water.

The mixture was extracted with dichloromethane, and dried over anhydrous sodium sulfate. The solvent was removed by evaporation. The residue was purified by NH silica gel column chromatography (chloroform) to give 5-(3-aminophenyl)-1,5,8,9,10,11-hexahydronaphtho[1,2-b][1,4]diazepine-2,4-dione as a colorless amorphous form (73 mg, 0.23 mmol).

The obtained amorphous form was dissolved in ethyl acetate (1.5 mL)-methanol (0.5 mL). To the solution was added 4M hydrogen chloride-ethyl acetate (0.056 mL) while stirring in ice-bath. The mixture was stirred overnight at room temperature. Precipitates were obtained by filtration, washed with ethyl acetate, and with hexane to give the titled compound as a yellow amorphous form (67 mg, yield 23%).

$^1$H NMR (CD$_3$OD, 400 MHz) δ: 1.7-2.1 (4H, m), 2.7-2.9 (4H, m), 3.25 (1H, d, J=12 Hz), 3.66 (1H, d, J=12 Hz), 6.70 (1H, d, J=8 Hz), 6.93 (1H, d, J=9 Hz), 7.22 (1H, d, J=8 Hz), 7.3-7.4 (2H, m), 7.55 (1H, t, J=8 Hz).

Example 9

5-[3-(2-Methyl-2H-tetrazol-5-yl)phenyl]-1,5,8,9,10,11-hexahydronaphtho[1,2-b][1,4]diazepine-2,4-dione 5-[3-(1-Methyl-1H-tetrazol-5-yl)phenyl]-1,5,8,9,10,11-hexahydronaphtho[1,2-b][1,4]diazepine-2,4-dione 5-[3-(1H-Tetrazol-5-yl)phenyl]-1,5,8,9,10,11-hexahydronaphtho[1,2-b][1,4]diazepine-2,4-dione sodium salt (40 mg, 0.10 mmol) obtained in Example 2 was used in a process similar to Example 6 to give 5-[3-(2-methyl-2H-tetrazol-5-yl)phenyl]-1,5,8,9,10,11-hexahydronaphtho[1,2-b][1,4]diazepine-2,4-dione as slightly brown crystal (18 mg, yield 46%) and 5-[3-(1-methyl-1H-tetrazol-5-yl)phenyl]-1,5,8,9,10,11-hexahydronaphtho[1,2-b][1,4]diazepine-2,4-dione as slightly brown crystal (3 mg, yield 8%).

5-[3-(2-Methyl-2H-tetrazol-5-yl)phenyl]-1,5,8,9,10,11-hexahydronaphtho[1,2-b][1,4]diazepine-2,4-dione $^1$H NMR (DMSO-d$_6$, 400 MHz) δ: 1.6-1.9 (4H, m), 2.5-2.8 (3H, m), 2.9-3.0 (1H, m), 3.07 (1H, d, J=12 Hz), 3.62 (1H, d, J=12 Hz), 4.41 (3H, s), 6.67 (1H, d, J=8 Hz), 6.89 (1H, d, J=8 Hz), 7.38 (1H, d, J=8 Hz), 7.63 (1H, t, J=8 Hz), 7.77 (1H, s), 8.00 (1H, d, J=7 Hz), 9.91 (1H, s).

5-[3-(1-Methyl-1H-tetrazol-5-yl)phenyl]-1,5,8,9,10,11-hexahydronaphtho[1,2-b][1,4]diazepine-2,4-dione $^1$H NMR (DMSO-d$_6$, 400 MHz) δ: 1.6-1.9 (4H, m), 2.5-2.8 (3H, m), 2.9-3.0 (1H, m), 3.08 (1H, d, J=12 Hz), 3.61 (1H, d, J=12 Hz), 4.16 (3H, s), 6.69 (1H, d, J=8 Hz), 6.90 (1H, d, J=8 Hz), 7.39 (1H, d, J=8 Hz), 7.67 (1H, t, J=8 Hz), 7.72 (1H, s), 7.80 (1H, d, J=7 Hz), 9.91 (1H, s).

Example 10

5-(4-Aminophenyl)-1,5,8,9,10,11-hexahydronaphtho[1,2-b][1,4]diazepine-2,4-dione (1) tert-Butyl 4-(1-nitro-5,6,7,8-tetrahydronaphthalen-2-ylamino)phenylcarbamate 1-Nitro-5,6,7,8-tetrahydronaphthalen-2-yl triflate (3.25 g, 10 mmol) and tert-butyl(4-aminophenyl)carbamate (2.08 g, 10 mmol) were used in a process similar to Example 1(1) to give the titled compound as a red solid (1.88 g, yield 49%).

$^1$H NMR (CDCl$_3$, 400 MHz) δ: 1.54 (9H, s), 1.7-1.8 (4H, m), 2.6-2.9 (4H, m), 3.81 (2H, br s), 6.40 (1H, br s), 6.9-7.1 (4H, m), 7.21 (1H, s), 7.2-7.4 (2H, m).

(2) tert-Butyl 4-(1-amino-5,6,7,8-tetrahydronaphthalen-2-ylamino)phenylcarbamate tert-Butyl 4-(1-nitro-5,6,7,8-tetrahydronaphthalen-2-ylamino)phenylcarbamate (1.87 g, 4.88 mmol) was used in a process similar to Example 1(2) to give the titled compound as orange crystal (1.42 g, yield 83%).

$^1$H NMR (CDCl$_3$, 400 MHz) δ: 1.50 (9H, s), 1.7-1.9 (4H, m), 2.4-2.9 (4H, m), 3.81 (2H, br s), 6.24 (1H, br s), 6.4-6.7 (3H, m), 6.8-6.9 (1H, m), 7.0-7.3 (2H, m).

(3) 5-(4-tert-Butoxycarbonylaminophenyl)-1,5,8,9,10,11-hexahydronaphtho[1,2-b][1,4]diazepine-2,4-dione 5-(4-tert-Butoxycarbonylaminophenyl)-1,5,8,9,10,11-hexahydronaphtho[1,2-b][1,4]diazepine-2,4-dione (1.42 g, 4.02 mmol) was used in a process similar to Example 1(3) to give the titled compound as a pale yellow amorphous form (0.38 g, yield 23%).

$^1$H NMR (CDCl$_3$, 400 MHz) δ: 1.51 (9H, s), 1.7-2.1 (4H, m), 2.5-2.8 (4H, m), 3.48 (2H, s), 6.53 (1H, bs), 6.69 (1H, d, J=8 Hz), 6.82 (1H, d, J=8 Hz), 7.1-7.2 (2H, m), 7.3-7.4 (2H, m), 7.52 (1H, br s).

(4) 5-(4-Aminophenyl)-1,5,8,9,10,11-hexahydronaphtho[1,2-b][1,4]diazepine-2,4-dione 5-(4-tert-Butoxycarbonylaminophenyl)-1,5,8,9,10,11-hexahydronaphtho[1,2-b][1,4]diazepine-2,4-dione (350 mg, 0.83 mmol) was used in a process similar to Example 8 to give the titled compound as white crystal (204 mg, yield 76%).

¹H NMR (CDCl₃, 400 MHz) δ: 1.7-2.1 (4H, m), 2.6-2.8 (4H, m), 3.4-3.5 (2H, m), 6.6-6.7 (2H, m), 6.74 (1H, d, J=8 Hz), 6.84 (1H, d, J=8 Hz), 6.9-7.0 (2H, m).

Example 11

5-(4-Methylaminophenyl)-1,5,8,9,10,11-hexahydronaphtho[1,2-b][1,4]diazepine-2,4-dione hydrochloride (1) N-[4-(2,4-Dioxo-1,2,3,4,8,9,10,11-octahydronaphtho[1,2-b][1,4]diazepine-5-yl)phenyl]-2-nitrobenzenesulfonamide 5-(4-Aminophenyl)-1,5,8,9,10,11-hexahydronaphtho[1,2-b][1,4]diazepine-2,4-dione (190 mg, 0.59 mmol) obtained in Example 10, o-nitrobenzenesulfonyl chloride (197 mg, 0.89 mmol), and dry pyridine (5 mL) were mixed. The mixture was stirred at 80° C. for 17 hours. Pyridine was removed by evaporation under reduced pressure. To the residue was added water. The mixture was extracted with ethyl acetate. The ethyl acetate layer was washed with dilute hydrochloric acid, and dried over anhydrous sodium sulfate. The solvent was removed by evaporation under reduced pressure. The residue was purified by silica gel column chromatography (chloroform) to give the titled compound as pale yellow crystal (233 mg, yield 78%).
¹H NMR (CDCl₃, 400 MHz) δ: 1.7-2.1 (4H, m), 2.6-2.8 (4H, m), 3.4-3.5 (2H, m), 6.60 (1H, d, J=8 Hz), 6.83 (1H, d, J=8 Hz), 7.1-7.2 (2H, m), 7.2-7.3 (2H, m), 7.47 (1H, s), 7.62 (1H, dt, J=1 Hz, 8 Hz), 7.71 (1H, dt, J=1 Hz, 8 Hz), 7.80 (1H, s), 7.86 (1H, dd, J=1 Hz, 8 Hz), 7.91 (1H, dd, J=1 Hz, 8 Hz).

(2) N-[4-(2,4-Dioxo-1,2,3,4,8,9,10,11-octahydronaphtho[1,2-b][1,4]diazepine-5-yl)phenyl]-N-methyl-2-nitrobenzenesulfonamide N-[4-(2,4-Dioxo-1,2,3,4,8,9,10,11-octahydronaphtho[1,2-b][1,4]diazepine-5-yl)phenyl]-2-nitrobenzenesulfonamide (150 mg, 0.3 mmol), methyl iodide (22 μL, 0.36 mmol), potassium carbonate (45 mg, 0.33 mmol), and dry dimethylformamide (3 mL) were mixed. The mixture was stirred at room temperature for 16 hours. The solvent was removed by evaporation under reduced pressure. To the residue was added water. The mixture was stirred at room temperature. Insoluble was obtained by filtration, washed with water, and air-dried overnight to give the titled compound as off-white crystal (112 mg, yield 73%).
¹H NMR (DMSO-d₆, 400 MHz) δ: 1.6-1.9 (4H, m), 2.6-2.8 (3H, m), 2.8-3.0 (1H, m), 3.04 (1H, d, J=12 Hz), 3.57 (1H, d, J=12 Hz), 6.62 (1H, d, J=8 Hz), 6.90 (1H, d, J=9 Hz), 7.16 (2H, d, J=9 Hz), 7.27 (2H, d, J=9 Hz), 7.72 (1H, dd, J=1 Hz, 8 Hz), 7.80 (1H, dt, J=1 Hz, 8 Hz), 7.91 (1H, dt, J=1 Hz, 8 Hz), 7.97 (1H, dd, J=1 Hz, 8 Hz), 9.90 (1H, s).

(3) 5-(4-Methylaminophenyl)-1,5,8,9,10,11-hexahydronaphtho[1,2-b][1,4]diazepine-2,4-dione hydrochloride N-[4-(2,4-Dioxo-1,2,3,4,8,9,10,11-octahydronaphtho[1,2-b][1,4]diazepine-5-yl)phenyl]-N-methyl-2-nitrobenzenesulfonamide (50 mg, 0.096 mmol) was dissolved in dry dimethylformamide (2 mL). To the solution were added potassium carbonate (40 mg, 0.29 mmol), and then thiophenol (12 μL, 0.12 mmol). The mixture was stirred overnight at room temperature. To the reaction mixture was added cold water. The mixture was extracted with ethyl acetate, washed with saturated brine, and dried over anhydrous sodium sulfate. The solvent was removed by evaporation under reduced pressure. The residue was purified by silica gel column chromatography (chloroform) to give 5-(4-methylaminophenyl)-1,5,8,9,10,11-hexahydronaphtho[1,2-b][1,4]diazepine-2,4-dione as a colorless amorphous form (32 mg, 0.095 mmol).

The obtained amorphous form was dissolved in ethyl acetate. To the solution was added 4M hydrogen chloride-ethyl acetate (25 μL). The mixture was stirred at room temperature for 1 hour. Precipitates were collected by filtration, washed with ethyl acetate, and with hexane to give the titled compound as off-white crystal (22 mg, yield 61%).
¹H NMR (DMSO-d₆, 400 MHz) δ: 1.6-1.9 (4H, m), 2.5-2.8 (3H, m), 2.72 (3H, s), 2.8-3.0 (1H, m), 3.00 (1H, d, J=12 Hz), 3.50 (1H, d, J=12 Hz), 6.64 (1H, d, J=8 Hz), 6.6-6.8 (2H, m), 6.85 (1H, d, J=9 Hz), 6.93 (2H, d, J=8 Hz), 9.82 (1H, s).

Example 12

5-(2,3-Dihydrobenzo[1,4]dioxin-6-yl)-1,5,8,9,10,11-hexahydronaphtho[1,2-b][1,4]diazepine-2,4-dione (1) 6-(1-Nitro-5,6,7,8-tetrahydronaphthalen-2-ylamino)-2,3-dihydrobenzo[1,4]dioxin 1-Nitro-5,6,7,8-tetrahydronaphthalen-2-yl triflate (3.25 g, 10 mmol) and 6-amino-2,3-dihydrobenzo[1,4]dioxin (1.51 g, 10 mmol) were used in a process similar to Example 1(1) to give the titled compound as red oil (3.20 g, yield 98%).
¹H NMR (CDCl₃, 400 MHz) δ: 1.7-1.8 (4H, m), 2.70 (2H, t, J=5 Hz), 2.80 (2H, t, J=5 Hz), 4.2-4.3 (4H, m), 6.60 (1H, dd, J=2 Hz, 8 Hz), 6.67 (1H, d, J=2 Hz), 6.81 (1H, d, J=8 Hz), 6.97 (1H, d, J=9 Hz), 7.00 (1H, d, J=9 Hz), 7.17 (1H, br s).

(2) 6-(1-Amino-5,6,7,8-tetrahydronaphthalen-2-ylamino)-2,3-dihydrobenzo[1,4]dioxin 6-(1-Nitro-5,6,7,8-tetrahydronaphthalen-2-ylamino)-2,3-dihydrobenzo[1,4]dioxin (3.20 g, 9.81 mmol) were used in a process similar to Example 1(2) to give the titled compound as pale pink crystal (2.58 g, yield 89%).
¹H NMR (CDCl₃, 400 MHz) δ: 1.7-1.9 (4H, m), 2.4-2.8 (4H, m), 4.1-4.2 (4H, m), 6.1-6.3 (2H, m), 6.4-6.6 (1H, m), 6.70 (1H, d, J=9 Hz), 6.85 (1H, d, J=9 Hz).

(3) 5-(2,3-Dihydrobenzo[1,4]dioxin-6-yl)-1,5,8,9,10,11-hexahydronaphtho[1,2-b][1,4]diazepine-2,4-dione 6-(1-Amino-5,6,7,8-tetrahydronaphthalen-2-ylamino)-2,3-dihydrobenzo[1,4]dioxin (1.06 g, 3.58 mmol) were used in a process similar to Example 1(3) to give the titled compound as a pale brown amorphous form (0.49 g, yield 38%).
¹H NMR (CDCl₃, 400 MHz) δ: 1.7-2.1 (4H, m), 2.5-2.8 (4H, m), 3.47 (2H, s), 4.2-4.3 (4H, m), 6.66 (1H, dd, J=2 Hz, 8 Hz), 6.7-6.8 (2H, m), 6.8-6.9 (2H, m), 7.6-7.7 (1H, m).

Example 13

5-(4-Methoxyphenyl)-1,5,8,9,10,11-hexahydronaphtho[1,2-b][1,4]diazepine-2,4-dione (1) N²-(4-Methoxyphenylamino)-5,6,7,8-tetrahydronaphthalene-1,2-diamine 1-Nitro-5,6,7,8-tetrahydronaphthalen-2-yl triflate (3.25 g, 10 mmol) and p-anisidine (1.23 g, 10 mmol) were used in a process similar to Example 3(1) to give the titled compound as an orange amorphous form (0.82 g, yield 31%).

$^1$H NMR (CDCl$_3$, 400 MHz) δ: 1.7-1.9 (4H, m), 2.4-2.6 (2H, m), 2.7-2.8 (2H, m), 3.75 (3H, s), 3.78 (2H, br s), 4.86 (1H, br s), 6.51 (1H, d, J=8 Hz), 6.6-6.7 (2H, m), 6.7-6.8 (2H, m), 6.85 (1H, d, J=8 Hz).

(2) 5-(4-Methoxyphenyl)-1,5,8,9,10,11-hexahydronaphtho[1,2-b][1,4]diazepine-2,4-dione N$^2$-(4-Methoxyphenylamino)-5,6,7,8-tetrahydronaphthalene-1,2-diamine (725 mg, 2.7 mmol) was used in a process similar to Example 1(3) to give the titled compound as a pale yellow amorphous form (224 mg, yield 25%).

$^1$H NMR (CDCl$_3$, 400 MHz) δ: 1.7-2.1 (4H, m), 2.5-2.8 (4H, m), 3.49 (2H, s), 3.81 (3H, s), 6.72 (1H, d, J=8 Hz), 6.84 (1H, d, J=8 Hz), 6.8-7.0 (2H, m), 7.1-7.2 (2H, m), 7.44 (1H, br s).

Example 14

5-(4-Hydroxyphenyl)-1,5,8,9,10,11-hexahydronaphtho[1,2-b][1,4]diazepine-2,4-dione 5-(4-Methoxyphenyl)-1,5,8,9,10,11-hexahydronaphtho[1,2-b][1,4]diazepine-2,4-dione (200 mg, 0.59 mmol) obtained in Example 13 was dissolved in dry dichloromethane (5 mL) while stirring in ice-bath. To the solution was dropwise added 1M boron tribromide-dichloromethane (1.2 mL). The mixture was stirred at room temperature for 16 hours and at 50° C. for 3 hours. The solvent was removed by evaporation under reduced pressure. To the residue was added cold water. The mixture was extracted with ethyl acetate, washed with saturated brine, and dried over anhydrous sodium sulfate. The solvent was removed by evaporation under reduced pressure. The residue was purified by silica gel column chromatography (chloroform/methanol=100/1) to give the titled compound as a white amorphous form (124 mg, yield 64%).

$^1$H NMR (DMSO-d$_6$, 400 MHz) δ: 1.6-1.9 (4H, m), 2.5-2.7 (3H, m), 2.8-3.0 (1H, m), 3.00 (1H, d, J=12 Hz), 3.50 (1H, d, J=12 Hz), 6.63 (1H, d, J=9 Hz), 6.7-6.8 (2H, m), 6.85 (1H, d, J=9 Hz), 6.9-7.0 (2H, m), 9.60 (1H, br s), 9.82 (1H, s).

Example 15

5-[4-(Isopropylcarbonylamino)phenyl]-1,5,8,9,10,11-hexahydronaphtho[1,2-b][1,4]diazepine-2,4-dione To a pyridine solution (0.5 mL) of 5-(4-aminophenyl)-1,5,8,9,10,11-hexahydronaphtho[1,2-b][1,4]diazepine-2,4-dione (20 mg, 0.062 mmol) obtained in Example 10 was added isobutyryl chloride (10 μL, 0.093 mmol). The mixture was stirred at 80° C. for 1 hour. To the reaction mixture was added aqueous solution of hydrochloric acid under cooling in ice-bath. The mixture was stirred for 20 minutes. Insoluble was collected by filtration, and washed with water. The residue was purified by silica gel column chromatography (chloroform/methanol=99/1) to give the titled compound as white powder (23 mg, yield 95%).

$^1$H NMR (CDCl$_3$, 400 MHz) δ: 1.24 (6H, d, J=7 Hz), 1.7-2.1 (4H, m), 2.4-2.6 (1H, m), 2.6-2.8 (4H, m), 3.4-3.6 (2H, m), 6.68 (1H, d, J=9 Hz), 6.82 (1H, d, J=9 Hz), 7.12 (2H, d, J=9 Hz), 7.35 (1H, br s), 7.51 (2H, d, J=9 Hz), 7.68 (1H, s).

Example 16

5-(3-Carbamoylphenyl)-1,5,8,10-tetrahydro-1H-indeno[6,7-b][1,4]diazepine-2,4-dione To 5-(3-cyanophenyl)-1,5,8,10-tetrahydro-1H-indeno[6,7-b][1,4]diazepine-2,4-dione (20 mg, 0.063 mmol) obtained in Example 4 was added 105% polyphosphoric acid (0.14 mL). The mixture was stirred at 115° C. for 1 hour. To the mixture was added cold water. The mixture was extracted with ethyl acetate. The ethyl acetate layer was washed with saturated brine, and dried over anhydrous sodium sulfate. The solvent was removed by evaporation under reduced pressure. The residue was recrystallized from ethyl acetate-hexane to give the titled compound as slightly yellow crystal (9 mg, yield 43%).

$^1$H NMR (DMSO-d$_6$, 400 MHz) δ: 2.0-2.1 (2H, m), 2.7-3.0 (3H, m), 3.08 (1H, d, J=12 Hz), 3.1-3.3 (1H, m), 3.63 (1H, d, J=12 Hz), 6.63 (1H, d, J=8 Hz), 6.99 (1H, d, J=8 Hz), 7.3-7.5 (2H, m), 7.51 (1H, t, J=8 Hz), 7.59 (1H, s), 7.83 (1H, d, J=8 Hz), 8.03 (1H, s), 10.21 (1H, s).

Example 17

1-Acetyl-5-[3-(5-methyl-[1,3,4]oxadiazol-2-yl)phenyl]-1,5,8,10-tetrahydro-1H-indeno[6,7-b][1,4]diazepine-2,4-dione

5-[3-(5-Methyl-[1,3,4]oxadiazol-2-yl)phenyl]-1,5,8,10-tetrahydro-1H-indeno[6,7-b][1,4]diazepine-2,4-dione By reference to synthetic example of 2-allyl-5-methyl-[1,3,4]oxadiazole [Chem Ber., 93, 2106 (1960)], 5-[3-(1H-tetrazol-5-yl)phenyl]-1,5,8,10-tetrahydro-1H-indeno[6,7-b][1,4]diazepine-2,4-dione (144 mg, 0.40 mmol) obtained in Example 5(1) was added acetic anhydride (5.8 mL), and the mixture was stirred at 100° C. for 2 hours. The mixture was cooled to room temperature. To the mixture was added cracked ice. The mixture was stirred for 30 minutes, and extracted with ethyl acetate. The ethyl acetate layer was washed with saturated aqueous solution of sodium hydrogencarbonate and then with saturated brine, and dried over anhydrous sodium sulfate. The solvent was removed by evaporation under reduced pressure. The residue was purified by silica gel column chromatography (ethyl acetate/hexane-1/1-3/1) to give 1-acetyl-5-[3-(5-methyl-[1,3,4]oxadiazol-2-yl)phenyl]-1,5,8,10-tetrahydro-1H-indeno[6,7-b][1,4]diazepine-2,4-dione as white powder (17 mg, yield 10%) and crude 5-[3-(5-methyl-[1,3,4]oxadiazol-2-yl)phenyl]-1,5,8,10-tetrahydro-1H-indeno[6,7-b][1,4]diazepine-2,4-dione. It was washed with ethyl acetate to give white crystal (41 mg, yield 28%).

1-Acetyl-5-[3-(5-methyl-[1,3,4]oxadiazol-2-yl)phenyl]-1,5,8,10-tetrahydro-1H-indeno[6,7-b][1,4]diazepine-2,4-dione $^1$H NMR (CDCl$_3$, 400 MHz) δ: 2.0-2.3 (2H, m), 2.60 (3H, s), 2.69 (3H, s), 2.7-2.9 (2H, m), 2.9-3.1 (2H, m), 3.49 (1H, d, J=13 Hz), 3.88 (1H, d, J=13 Hz), 6.81 (1H, d, J=8 Hz), 7.17 (1H, d, J=8 Hz), 7.29 (1H, d, J=8 Hz), 7.49 (1H, t, J=8 Hz), 7.9-8.1 (2H, m).

5-[3-(5-Methyl-[1,3,4]oxadiazol-2-yl)phenyl]-1,5,8,10-tetrahydro-1H-indeno[6,7-b][1,4]diazepine-2,4-dione $^1$H NMR (CDCl$_3$, 400 MHz) δ: 2.2-2.3 (2H, m), 2.60 (3H, s), 2.9-3.0 (4H, m), 3.5-3.6 (2H, m), 6.72 (1H, d, J=8 Hz), 6.96 (1H, d, J=8 Hz), 7.44 (1H, d, J=9 Hz), 7.54 (1H, t, J=8 Hz), 7.65 (1H, s), 7.84 (1H, s), 7.95 (1H, d, J=8 Hz).

Example 18

5-[3-(5-Phenyl[1,3,4]oxadiazol-2-yl)phenyl]-1,5,8,10-tetrahydro-1H-indeno[6,7-b][1,4]diazepine-2,4-dione 5-[3-(1H-Tetrazol-5-yl)phenyl]-1,5,8,10-tetrahydro-1H-indeno[6,7-b][1,4]diazepine-2,4-dione (36 mg, 0.10 mmol) and benzoic anhydride (226 mg, 1.00 mmol) were used in a process similar to Example 17 to give the titled compound as white crystal (11 mg, yield 25%).

$^1$H NMR (DMSO-d$_6$, 400 MHz) δ: 2.0-2.2 (2H, m), 2.7-3.0 (3H, m), 3.12 (1H, d, J=12 Hz), 3.1-3.3 (1H, m), 3.68 (1H, d, J=12 Hz), 6.72 (1H, d, J=8 Hz), 7.01 (1H, d, J=8 Hz), 7.40 (1H, d, J=7 Hz), 7.6-7.7 (4H, m), 7.98 (1H, s), 8.0-8.2 (3H, m), 10.24 (1H, s).

Example 19

Experimental Procedure

P2X$_4$ receptor antagonism of the compound of the present invention was measured as described below.

1321N1 cells stably expressing human P2X$_4$ receptors were plated in 96-well assay plate and cultured for 24 hours at 37° C. in an atmosphere of 5% CO$_2$ for intracellular calcium assay. Fura-2 AM calcium fluorescent indicator was used for the intracellular calcium assay. Fura-2 AM was dissolved in an assay buffer, and the solution was loaded onto cells. The obtained plate was used for fluorescent assay.

Test compounds were treated to cells for 15 minutes before the addition of ATP, and the response to intracellular calcium influx induced by addition of ATP was monitored by a micro plate reader. The fluorescence ratio of excitations wavelengths of 340 nm and 380 nm was used as the index of intracellular calcium change. The inhibition activities of the test compounds were calculated by comparison with the absence of the test compound (control).

(Experimental Results)

TABLE 19

| Test compound | Inhibition activities (IC$_{50}$ μM) |
|---|---|
| Example 2 | 0.36 |
| Example 3 | 3.9 |
| Example 5 | 0.97 |

As is evident from Table 19, the compound of the present invention described in Example 2 has excellent P2X$_4$ receptor antagonism.

Example 20

P2X$_4$ receptor antagonism of the compound of the present invention was measured in the same manner as in Example 19.

The results are set forth in Table 20.

TABLE 20

| Test compound | Inhibition activities (IC$_{50}$ μM) |
|---|---|
| Example 8 | 4.0 |
| Example 9 | 2.6 |
| Example 10 | 6.1 |
| Example 11 | 3.3 |
| Example 13 | 6.9 |
| Example 14 | 3.8 |
| Example 17 | 1.9 |

As is evident from Table 20, the compounds of the present invention have excellent P2X$_4$ receptor antagonism.

The invention claimed is:

1. A compound having the following formula (II) or a pharmacologically acceptable salt thereof:

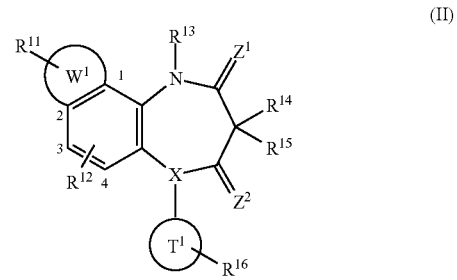

(II)

wherein each of R$^{11}$ and R$^{12}$ independently is hydrogen, a C$_{1-8}$ alkyl group, a C$_{2-8}$ alkenyl group, a C$_{1-8}$ alkoxy group, a C$_{1-8}$ alkyl group having one to three halogen atoms, a C$_{1-8}$ alkoxy group having one to three halogen atoms, a halogen atom, hydroxyl, nitro, cyano, amino, a C$_{1-8}$ alkylamino group, a C$_{2-8}$ dialkylamino group, a C$_{2-8}$ acylamino group, a C$_{2-8}$ acylamino group having one to three halogen atoms, a C$_{1-8}$ alkylsulfonylamino group, carboxyl, a C$_{2-8}$ acyl group, an alkoxycarbonyl group comprising a C$_{1-8}$ alkoxy moiety, carbamoyl, a C$_{1-8}$ alkylthio group, a C$_{1-8}$ alkylsulfinyl group, a C$_{1-8}$ alkylsulfonyl group, or sulfamoyl;

R$^{13}$ is hydrogen, a C$_{14}$ alkyl group, a C$_{2-8}$ alkenyl group, a C$_{2-8}$ acyl group, a C$_{1-8}$ alkyl group having one to three halogen atoms, or a C$_{1-3}$ alkyl group having phenyl;

each of R$^{14}$ and R$^{15}$ independently is hydrogen, a C$_{1-8}$ alkyl group, a C$_{1-8}$ alkyl group having one to three halogen atoms, a halogen atom, hydroxyl, nitro, cyano, amino, or a C$_{1-3}$ alkyl group having phenyl;

R$^{16}$ is hydrogen, a C$_{1-8}$ alkyl group, a C$_{2-8}$ alkenyl group, a C$_{1-8}$ alkoxy group, a C$_{1-8}$ alkyl group having one to three halogen atoms, a C$_{1-8}$ alkoxy group having one to three halogen atoms, a halogen atom, hydroxyl, nitro, cyano, amino, a C$_{1-8}$ alkylamino group, a C$_{2-8}$ dialkylamino group, a C$_{2-8}$ acylamino group, a C$_{2-8}$ acylamino group having one to three halogen atoms, a C$_{1-8}$ alkylsulfonylamino group, carboxyl, a C$_{2-8}$ acyl group, an alkoxycarbonyl group comprising a C$_{1-8}$ alkoxy moiety, carbamoyl, a C$_{1-8}$ alkylthio group, a C$_{1-8}$ alkylsulfinyl group, a C$_{1-8}$ alkylsulfonyl group, a C$_{3-8}$ alkoxycarbonylamino group, sulfamoyl, phenyl optionally having one or more substituents, or a heterocyclic group optionally having one or more substituents;

Ring W$^1$ is a five-membered to eight-membered non-aromatic ring optionally comprising one or two heteroatoms selected from N, S, and O, and being condensed with the benzene ring at the positions of 1 and 2 of the benzene ring;

Ring $T^1$ is an aromatic ring selected from the group consisting of benzene ring, naphthalene ring, thiophene ring, pyridine ring, pyrimidine ring, indole ring, indazole ring, benzotriazole ring, benzisoxazole ring, benzimidazole ring, and quinoline ring;

X is N; and each of $Z^1$ and $Z^2$ is O.

2. A compound or a pharmacologically acceptable salt thereof defined in claim 1, wherein $R^{11}$ is hydrogen, a $C_{1-8}$ alkyl group, a $C_{2-8}$ alkenyl group, a $C_{1-8}$ alkyl group having one to three halogen atoms, a halogen atom, hydroxyl, amino, a $C_{1-8}$ alkylamino group, a $C_{2-8}$ dialkylamino group, or a $C_{2-8}$ acylamino group.

3. A compound or a pharmacologically acceptable salt thereof defined in claim 1, wherein $R^{12}$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, or a $C_{2-8}$ acylamino group having one to three halogen atoms.

4. A compound or a pharmacologically acceptable salt thereof defined in claim 1, wherein $R^{13}$ is hydrogen, a $C_{1-8}$ alkyl group, or a $C_{1-8}$ alkyl group having one to three halogen atoms.

5. A compound or a pharmacologically acceptable salt thereof defined in claim 1, wherein each of $R^{14}$ and $R^{15}$ independently is hydrogen, a $C_{1-8}$ alkyl group, or a $C_{1-8}$ alkyl group having one to three halogen atoms.

6. A compound or a pharmacologically acceptable salt thereof defined in claim 1, wherein $R^{16}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, or a heterocyclic group optionally having one or more substituents.

7. A compound or a pharmacologically acceptable salt thereof defined in claim 1, wherein $R^{16}$ is a heterocyclic group optionally having one or more substituents, said heterocyclic group being tetrazolyl, triazolyl, pyridyl, pyrazolyl, oxadiazolyl, isoxazolyl, pyrrolyl, pyrrolidinyl, imidazolyl, oxazolyl, or thiazolyl, and said substituents being selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

8. A compound or a pharmacologically acceptable salt thereof defined in claim 1, wherein $R^{16}$ is a heterocyclic group optionally having one or more substituents, said heterocyclic group being tetrazolyl, triazolyl, pyridyl, imidazolyl, oxazolyl, or thiazolyl, and said substituents being selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, cyano, and amino.

9. A compound or a pharmacologically acceptable salt thereof defined in claim 1, wherein the ring shown below is tetrahydronaphthalene, indan, indoline, tetrahydroquinoline, or tetrahydroisoquinoline.

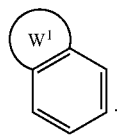

10. A compound or a pharmacologically acceptable salt thereof defined in claim 1, wherein the ring shown below is benzene.

11. A compound having the following formula (III) or a pharmacologically acceptable salt thereof:

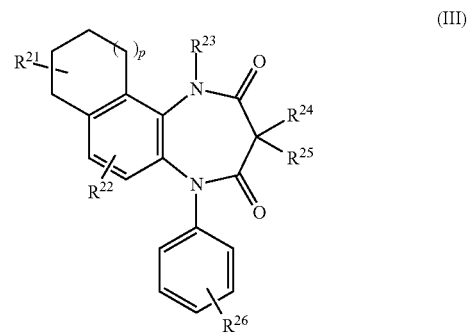

(III)

wherein each of $R^{21}$ and $R^{22}$ independently is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, or sulfamoyl;

$R^{23}$ is hydrogen, a $C_{1-8}$ alkyl group, a $C_{2-8}$ alkenyl group, a $C_{2-8}$ acyl group, a $C_{1-8}$ alkyl group having one to three halogen atoms, or a $C_{1-3}$ alkyl group having phenyl;

each of $R^{24}$ and $R^{25}$ independently is hydrogen, a $C_{1-8}$ alkyl group, a $C_{1-8}$ alkyl group having one to three halogen atoms, a halogen atom, hydroxyl, nitro, cyano, amino, or a $C_{1-3}$ alkyl group having phenyl;

$R^{26}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, a $C_{2-8}$ acylamino group having one to three halogen atoms, a $C_{1-8}$ alkylsulfonylamino group, carboxyl, a $C_{2-8}$ acyl group, an alkoxycarbonyl group comprising a $C_{1-8}$ alkoxy moiety, carbamoyl, a $C_{1-8}$ alkylthio group, a $C_{1-8}$ alkylsulfinyl group, a $C_{1-8}$ alkylsulfonyl group, a $C_{3-8}$ alkoxycarbonylamino group, sulfamoyl, phenyl optionally having one or more substituents, or a heterocyclic group optionally having one or more substituents; and p is 0 or 1.

12. A compound or a pharmacologically acceptable salt thereof defined in claim 11, wherein $R^{21}$ is hydrogen, a $C_{1-8}$ alkyl group, a $C_{2-8}$ alkenyl group, a $C_{1-8}$ alkyl group having one to three halogen atoms, a halogen atom, hydroxyl, amino, a $C_{1-8}$ alkylamino group, a $C_{2-8}$ dialkylamino group, or a $C_{2-8}$ acylamino group.

13. A compound or a pharmacologically acceptable salt thereof defined in claim 11, wherein $R^{22}$ is hydrogen, a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, a $C_{2-8}$ acylamino group, or a $C_{2-8}$ acylamino group having one to three halogen atoms.

14. A compound or a pharmacologically acceptable salt thereof defined in claim 11, wherein $R^{23}$ is hydrogen, a $C_{1-8}$ alkyl group, or a $C_{1-8}$ alkyl group having one to three halogen atoms.

15. A compound or a pharmacologically acceptable salt thereof defined in claim 11, wherein each of $R^{24}$ and $R^{25}$ independently is hydrogen, a $C_{1-8}$ alkyl group, or a $C_{1-8}$ alkyl group having one to three halogen atoms.

16. A compound or a pharmacologically acceptable salt thereof defined in claim 11, wherein $R^{26}$ is hydrogen, a $C_{1-8}$ alkyl group, a $C_{2-8}$ alkenyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, a $C_{2-8}$ dialkylamino group, or a heterocyclic group optionally having one or more substituents.

17. A compound or a pharmacologically acceptable salt thereof defined in claim 11, wherein $R^{26}$ is a heterocyclic group optionally having one or more substituents, said heterocyclic group being tetrazolyl, triazolyl, pyridyl, pyrazolyl, oxadiazolyl, isoxazolyl, pyrrolyl, pyrrolidinyl, imidazolyl, oxazolyl, or thiazolyl, and said substituents being selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, nitro, cyano, amino, a $C_{1-8}$ alkylamino group, and a $C_{2-8}$ dialkylamino group.

18. A compound or a pharmacologically acceptable salt thereof defined in claim 11, wherein $R^{26}$ is a heterocyclic group optionally having one or more substituents, said heterocyclic group being tetrazolyl, triazolyl, pyridyl, imidazolyl, oxazolyl, or thiazolyl, and said substituents being selected from the group consisting of a $C_{1-8}$ alkyl group, a $C_{1-8}$ alkoxy group, a $C_{1-8}$ alkyl group having one to three halogen atoms, a $C_{1-8}$ alkoxy group having one to three halogen atoms, a halogen atom, hydroxyl, cyano, and amino.

19. A compound selected from a group consisting of

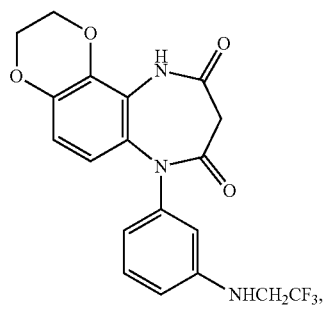

-continued

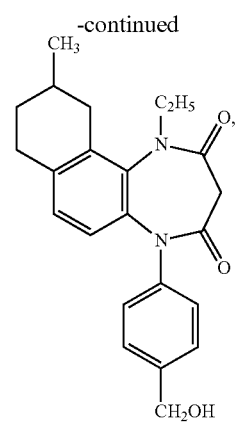

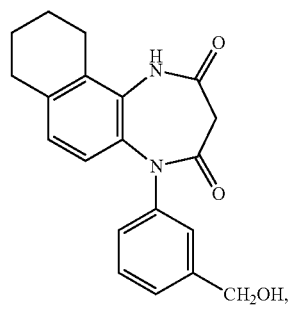

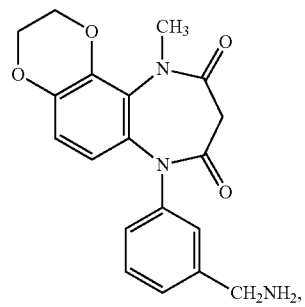

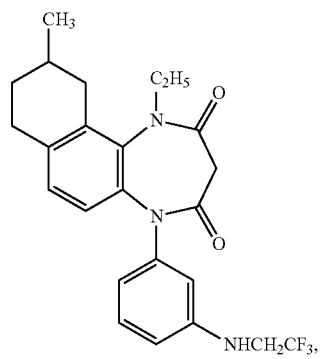

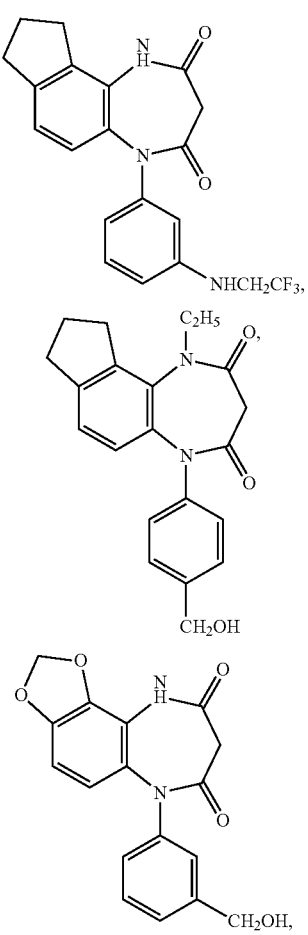

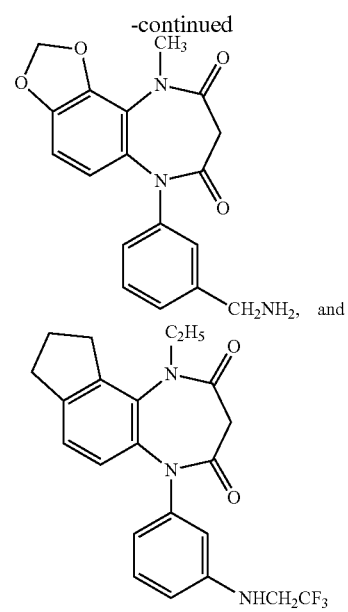

or a pharmacologically acceptable salt thereof.

20. 5-(2,3-dihydrobenzo[1,4]dioxin-6-yl)-1,5,8,9,10,11-hexahydronaphtho[1,2-b][1,4]diazepine-2,4-dione or a pharmacologically acceptable salt thereof.

21. A pharmaceutical composition comprising an effective amount of a compound according to claim 1 or a pharmacologically acceptable salt thereof and a pharmaceutically acceptable carrier.

22. A method of treating neuropathic pain comprising administering an effective amount of a compound according to claim 1 or a pharmacologically acceptable salt thereof to a patient in need thereof.

* * * * *